US011280743B2

(12) United States Patent
Takahashi

(10) Patent No.: US 11,280,743 B2
(45) Date of Patent: *Mar. 22, 2022

(54) APPARATUS AND METHOD FOR ASSESSING OPTICAL QUALITY OF GEMSTONES

(71) Applicant: GEMOLOGICAL INSTITUTE OF AMERICA, INC. (GIA), Carlsbad, CA (US)

(72) Inventor: Hiroshi Takahashi, Fort Lee, NJ (US)

(73) Assignee: Gemological Institute of America, Inc. (GIA), Carlsbad, CA (US)

(*) Notice: Subject to any disclaimer, the term of this patent is extended or adjusted under 35 U.S.C. 154(b) by 73 days.

This patent is subject to a terminal disclaimer.

(21) Appl. No.: 16/697,164

(22) Filed: Nov. 26, 2019

(65) Prior Publication Data
US 2020/0096453 A1     Mar. 26, 2020

Related U.S. Application Data

(60) Continuation of application No. 15/588,389, filed on May 5, 2017, now Pat. No. 10,533,951, which is a
(Continued)

(51) Int. Cl.
*G01N 21/87*     (2006.01)
*G01N 21/25*     (2006.01)
(Continued)

(52) U.S. Cl.
CPC ........... *G01N 21/87* (2013.01); *G01N 21/255* (2013.01); *G01N 33/381* (2013.01); *G01N 21/88* (2013.01);
(Continued)

(58) Field of Classification Search
CPC ...... G01N 21/255; G01N 21/87; G01N 21/88; G01N 2201/061; G01N 2201/0631;
(Continued)

(56) References Cited

U.S. PATENT DOCUMENTS

| 5,615,005 | A  | 3/1997 | Valente  |
| 6,239,867 | B1 | 5/2001 | Aggarwal |

(Continued)

FOREIGN PATENT DOCUMENTS

| CN | 1135040 A | 11/1996 |
| CN | 1196121 A | 10/1998 |

(Continued)

OTHER PUBLICATIONS

Moses et al., "A Foundation for Grading the Overall Cut Quality of Round Brilliant Cut Diamonds", Gems & Gemology, Grading Overall Cut Quality, Fall 2004, vol. 40, No. 3, Fall 2004, 27 pages. https://www.gia.edu/gems-gemology/fall-2004-grading-cut-quality-brilliant-diamond-moses.

*Primary Examiner* — Hina F Ayub
(74) *Attorney, Agent, or Firm* — DLA Piper LLP (US)

(57) ABSTRACT

Provided herein is an apparatus for assessing a color characteristic of a gemstone. The apparatus comprises an optically opaque platform for supporting a sample gemstone to be assessed, a daylight-approximating light source to provide uniform illumination to the gemstone, an image capturing component, and a telecentric lens positioned to provide an image of the illuminated gemstone to the image capturing component. Also provided are methods of color analysis based on images collected using such an apparatus.

16 Claims, 18 Drawing Sheets

Related U.S. Application Data division of application No. 14/673,776, filed on Mar. 30, 2015, now Pat. No. 9,678,018.

(51) Int. Cl.
  *G01N 33/38* (2006.01)
  *G01N 21/88* (2006.01)

(52) U.S. Cl.
  CPC . *G01N 2201/061* (2013.01); *G01N 2201/065* (2013.01); *G01N 2201/0631* (2013.01); *G01N 2201/0634* (2013.01); *G01N 2201/0638* (2013.01)

(58) Field of Classification Search
  CPC ... G01N 2201/0634; G01N 2201/0638; G01N 2201/065; G01N 33/381
  See application file for complete search history.

(56) References Cited

U.S. PATENT DOCUMENTS

| | | |
|---|---|---|
| 6,473,164 B1 | 10/2002 | De Jong |
| 6,980,283 B1 | 12/2005 | Aggarwal |
| 7,260,544 B1 | 8/2007 | Reinitz et al. |
| 7,411,663 B2 | 8/2008 | Van de Velde |
| 7,420,657 B2 | 9/2008 | Sasian |
| 7,571,060 B2 | 8/2009 | Blodgett |
| 8,116,552 B2 | 2/2012 | Lapa et al. |
| 8,436,986 B2 | 5/2013 | Graham et al. |
| 8,705,018 B2 | 4/2014 | Benderly et al. |
| 9,222,893 B2 | 12/2015 | Hornabrook et al. |
| 9,250,193 B2 | 2/2016 | Smith |
| 9,322,785 B2 | 4/2016 | Smith et al. |
| 9,435,747 B2 | 9/2016 | Song et al. |
| 9,618,443 B2 | 4/2017 | Smith et al. |
| 9,678,018 B2 | 6/2017 | Takahashi |
| 10,533,951 B2 | 1/2020 | Takahashi |
| 2003/0107722 A1 | 6/2003 | Klingler |
| 2004/0072137 A1 | 4/2004 | Lapa et al. |
| 2005/0117145 A1 | 6/2005 | Altman et al. |
| 2005/0187831 A1 | 8/2005 | Gershburg et al. |
| 2007/0053003 A1* | 3/2007 | Loce ............... H04N 1/40075 358/3.06 |
| 2007/0153256 A1* | 7/2007 | Liu ..................... G01J 3/465 356/30 |
| 2007/0285650 A1 | 12/2007 | Kerner et al. |
| 2008/0225266 A1 | 9/2008 | Van De Velde et al. |
| 2010/0015438 A1 | 1/2010 | Williams et al. |
| 2010/0085299 A1 | 4/2010 | Yoon et al. |
| 2010/0085635 A1 | 4/2010 | Verboven et al. |
| 2010/0127180 A1 | 5/2010 | Lifshitz et al. |
| 2011/0299063 A1 | 12/2011 | Ninomiya et al. |
| 2012/0007971 A1 | 1/2012 | Schnitzer et al. |
| 2012/0179290 A1 | 7/2012 | Lo |
| 2013/0226008 A1 | 8/2013 | Dana et al. |
| 2014/0043621 A1 | 2/2014 | Ahner et al. |
| 2014/0227774 A1 | 8/2014 | Guthrie et al. |
| 2017/0000406 A1* | 1/2017 | Schnidar ............ G06T 7/0016 |
| 2017/0241913 A1 | 8/2017 | Gu |

FOREIGN PATENT DOCUMENTS

| | | |
|---|---|---|
| CN | 1290343 A | 4/2001 |
| CN | 1304035 A | 7/2001 |
| CN | 1398346 A | 2/2003 |
| CN | 1478200 A | 2/2004 |
| CN | 1505757 A | 6/2004 |
| CN | 1902474 A | 1/2007 |
| CN | 101263381 A | 9/2008 |
| CN | 102216760 A | 10/2011 |
| CN | 102596433 A | 7/2012 |
| CN | 101652654 B | 10/2012 |
| CN | 102884419 A | 1/2013 |
| CN | 102967604 A | 3/2013 |
| GB | 2500259 A | 9/2013 |
| JP | H07239303 A | 9/1995 |
| JP | 2002516992 A | 6/2002 |
| JP | 2013034725 A | 2/2013 |
| JP | 2013510302 A | 3/2013 |
| JP | 2015057791 A | 3/2015 |
| WO | WO9704303 A1 | 2/1997 |
| WO | WO9934197 A1 | 7/1999 |
| WO | WO02082063 A1 | 10/2002 |

* cited by examiner

| Mask | L | a | b | C | H |
|---|---|---|---|---|---|
| Sample 1 100% | 0.951 | -0.048 | 0.504 | 0.507 | 95.472 |

FIG. 12A

| Sample Number | Visual Grade | Instrument Grade | Mask Applied |
|---|---|---|---|
| 1 | D | D | 100% |
| 2 | F | F | 100% |
| 3 | J | J | 100% |

FIG. 12B

| Sample Number | Color | Visual Grade | Instrument Grade | Mask Applied |
|---|---|---|---|---|
| 4 | bluish | E | E | 100% |
| 5 | pinkish | F | F | 100% |
| 6 | brown | Y/Z | Y/Z | 100% |
| 7 | greenish yellow | F | F | 100% |

FIG. 13

| Sample Number | Shape | Visual Grade | Instrument Grade | Mask Applied |
|---|---|---|---|---|
| 8 | marquise | F | F | 100% |
| 9 | emerald | G | G | 100% |
| 10 | cushion | F | F | 100% |

FIG. 14A

| | Mask | L | a | b | C | H |
|---|---|---|---|---|---|---|
| Sample 9 | 100% | 0.952 | -0.306 | 2.032 | 2.055 | 98.576 |

FIG. 14B

| Sample Number | Shape | Visual Grade | Instrument Grade with Regular Mask | | Instrument Grade with Modified Mask | |
|---|---|---|---|---|---|---|
| | | | Mask | Grade | Mask | Grade |
| 11 | high depth | J | 100% | L | Triangular | J |
| 12 | low depth | H | 100% | I | 50% | H |

FIG. 15

APPARATUS AND METHOD FOR ASSESSING OPTICAL QUALITY OF GEMSTONES

CROSS REFERENCE TO RELATED APPLICATION

This application is a continuation of and claims priority to U.S. patent application Ser. No. 15/588,389, filed on May 5, 2017 which in turn claims priority to U.S. patent application Ser. No. 14/673,776 (U.S. Pat. No. 9,678,018), filed on Mar. 30, 2015 and entitled "APPARATUS AND METHOD FOR ASSESSING OPTICAL QUALITY OF GEMSTONES," which is hereby incorporated by reference herein in its entirety.

FIELD

The apparatus and methods disclosed herein generally relate to assessment of optical qualities of gemstones, in particular cut gemstones. In particular, the apparatus and methods relate to assessment of color quality of cut diamonds. The apparatus and methods disclosed herein further relate to digital image processing based on color component analysis.

BACKGROUND

Diamonds and other gemstones are often analyzed and graded by multiple trained and skilled individuals, based upon their visual appearance. For example, the foundation of diamond analysis comprises analysis of the Four C's (color, clarity, cut and carat weight), two of which, color and clarity, have been traditionally evaluated by human inspection. In particular, a diamond's visual appearance to the human eye under natural or daylight-approximating light is a primary indicator of the quality of the diamond. Accordingly, because diamond quality is substantially based on human visual perception, analysis and grading requires the exercise of judgment, the formation of opinions and the ability to draw fine distinctions based on visual comparisons.

A process of inspection and analysis is often time-consuming, involving multiple rounds of inspections, measurements and checks by each trained and experienced individual. The process also involves quality control and may include a variety of non-destructive tests to identify treatments, fillings or other defects that may affect the quality of a specimen. Finally, the process includes intensive visual comparison of the diamond with a reference set of diamond master stones that serve as a historical standard with respect to diamond color.

Instruments have been created to improve efficiency and to permit gemstone analysis in the absence of trained and experienced individuals. However, even though the performance of these instruments is generally good, there are issues that continue to cause concerns. Most significantly, there appears to be good evidence that certain stones consistently give significantly different results when measured on such instruments in comparison to visual grading by experienced human graders.

What is need are apparatus and methods that can consistently and accurately approximate gemstone analysis and grading (e.g., color of diamonds) by trained and experienced individuals.

SUMMARY

In one aspect, provided herein is an apparatus for assessing a color characteristic of a gemstone. The apparatus comprises an optically opaque platform, where the platform has a surface configured for supporting a gemstone to be assessed; a daylight-approximating light source shaped to at least partially enclose the platform, where the light source is designed to provide uniform diffused illumination to the gemstone on the platform; an image capturing component, where the image capturing component is positioned at a predetermined angle relative to the platform surface that supports the gemstone, and where the image capturing component and platform are configured to rotate relative to each other; and a telecentric lens positioned to provide an image of the illuminated gemstone to the image capturing component.

In another aspect, provided herein is an apparatus for assessing a color characteristic of a gemstone. The apparatus comprises an optically opaque platform, where the platform has a surface configured for supporting a gemstone to be assessed; a daylight-approximating light source; a diffuser, where the diffuser and the daylight-approximating light source are coupled to provide uniform diffused illumination to the gemstone on the platform; an image capturing component, where the image capturing component is positioned at a predetermined angle relative to the platform surface that supports the gemstone, and wherein the image capturing component and platform are configured to rotate relative to each other; and a telecentric lens positioned to provide an image of the illuminated gemstone to the image capturing component.

In some embodiments, the apparatus further comprises a reflector device having an inner surface that is at least partially spherical and comprises a reflective material, where the reflector device at least partially covers the daylight-approximating light source and platform surface, and directs light from the light source towards the gemstone positioned on the platform surface. In some embodiments, the inner surface of the reflector device has a hemispherical shape.

In some embodiments, the telecentric lens comprises an object-space telecentric lens, or a double telecentric lens. In some embodiments, the telecentric lens is a double telecentric lens.

In some embodiments, the platform is configured to rotate about a rotational axis that is perpendicular to the surface of the platform where the gemstone is supported. In some embodiments, the platform is configured to rotate 360 degrees around a rotational axis. In some embodiments, the platform is a flat circular platform, and where the rotational axis is through the center of the circular platform.

In some embodiments, the predetermined angle between the image capturing component and the platform surface is between approximately zero and approximately 45 degrees. In some embodiments, the predetermined angle between the image capturing component and the platform surface is between approximately 10 and approximately 35 degrees.

In some embodiments, the reflective material on the at least partially spherical inner surface of the reflector device is selected from the group consisting of polytetrafluoroethylene (PTFE), Spectralon™, barium sulfate, Gold, Magnesium Oxide, and combinations thereof.

In some embodiments, the platform surface comprises a reflective material. In some embodiments, the platform surface comprises a diffuse reflective material. In some embodiments, the platform surface comprises a white diffuse reflective material. In some embodiments, the platform surface comprises a Teflon™ material.

In some embodiments, the platform is made of a material selected from the group consisting of polytetrafluoroethylene (PTFE), Spectralon™, barium sulfate, Gold, Magnesium Oxide, and combinations thereof.

In some embodiments, the daylight-approximating light source is configured as a ring light surrounding the platform surface. In some embodiments, the daylight-approximating light source is selected from the group consisting of one or more halogen lamps with a color balancing filter, multiple light emitting diodes arranged in a ring-like structure surrounding the platform surface, fluorescence lamp, Xe lamp, Tungsten lamp, metal halide lamp, laser-induced white light (LDLS), and combinations thereof.

In some embodiments, the image capturing component is selected from the group consisting of a color camera, a CCD camera, and one or more CMOS sensor arrays.

In some embodiments, image capturing component captures a plurality of color images of the illuminated gemstone, each taken when the image capturing component and the platform surface are at a different relative rotational position.

In some embodiments, the apparatus further comprises a computer readable medium for storing the images collected by the image capturing component. In some embodiments, where the color characteristic of the gemstone is a color grade.

In one aspect, provided herein is a method of assessing a color characteristic of a sample gemstone. The method comprises the steps of (i) determining a proportion or shape characteristic of a sample gemstone based on a plurality of color images, where each image of the plurality of color images includes a full image of the sample gemstone, is taken at a unique image angle, and comprises a plurality of pixels; (ii) selecting a defined area corresponding to the proportion or shape characteristic for further color analysis, where the defined area is within the full image of the sample gemstone in each image of the plurality of color images; (iii) quantifying individual color components in each pixel in the defined area in each image of the plurality of color images, thereby converting values for individual color components to one or more parameters representing the color characteristic of each pixel; (iv) determining an average value for each of the one or more parameters for all pixels in the defined area in all images of the plurality of color image; (v) calculating one or more color scores of a sample gemstone based on the average values of the one or more parameters of all pixels in the defined area in all images of the plurality of color images; and (vi) assessing the color characteristic of the sample gemstone by comparing the one or more color scores to values of corresponding color scores of one or more control gemstones classified to be in the pre-determined category, thereby assigning a color grade to the sample gemstone.

In some embodiments, the sample gemstone is a diamond.

In some embodiments, the proportion or shape characteristic of the sample gemstone is determined using outline masks created based on the plurality of color images, wherein each outline mask has an open area corresponding to the full image of the sample gemstone in each image in the plurality of color images.

In some embodiments, each outline mask has a width and a height. In some embodiments, the proportion or shape characteristic is $width_{max}/width_{min}$, wherein $width_{max}$ is the maximum width identified for the outline masks and $width_{min}$ is the minimum width diamond width identified for the outline masks.

In some embodiments, the proportion or shape characteristic is $(height/width)_{min}$, wherein $(height/width)_{min}$ is the minimum aspect ratio identified for the outline masks.

In some embodiments, the defined area is selected using a virtual mask having an open area that corresponds to a portion of the open area in the corresponding outline mask. In some embodiments, the open area of the virtual mask corresponds to 30% to 100% of the total area of the open area of the outline mask.

In some embodiments, the individual color components comprise the colors red (R), green (G) and blue (B).

In some embodiments, average values for one individual color component are calculated by averaging the values corresponding to the individual color component of each pixel in the defined area.

In some embodiments, the method further comprises the step of collecting the plurality of color images of the sample gemstone using an image capturing component at uniquely different image angles, where an image angle defines the relative angular position between the image capturing component and a predetermined reference position on a platform surface upon which the sample gemstone is positioned.

In some embodiments, the image capturing component receives each image of the illuminated gemstone in the plurality of color images from a telecentric lens. In some embodiments, the telecentric lens comprises an object-space telecentric lens, or a double telecentric lens. In some embodiments, the telecentric lens is a double telecentric lens.

In some embodiments, the method of color assessment further comprises a step of collecting a new plurality of color images of the sample gemstone using the image capturing component at the image angle and the predetermined reference position on the platform surface. In such embodiments, there is a time gap between the time when the plurality of color images is collected and the time when the new plurality of color images is collected.

In some embodiments, a new color grade is assigned to the sample gemstone based on the new plurality of color images by applying steps (i) through (vi). The new color grade and the previously determined color grade are then compared to evaluate color change over the time gap.

In some embodiments, the time gap is between 2 minutes and 2 hours.

It will be understood that any of the embodiments disclosed herein can be applied, alone or in combination, to all aspects of the invention.

BRIEF DESCRIPTION OF THE DRAWINGS

Those of skill in the art will understand that the drawings, described below, are for illustrative purposes only. The drawings are not intended to limit the scope of the present teachings in any way.

FIG. 12A depicts exemplary color grading calculations.

FIG. 12B depicts exemplary color grading results.

FIG. 13 depicts exemplary color grading results.

FIG. 14A depicts exemplary color grading results.

FIG. 14B depicts exemplary color grading calculations.

FIG. 15 depicts exemplary color grading results.

DETAILED DESCRIPTION

Figure 1:
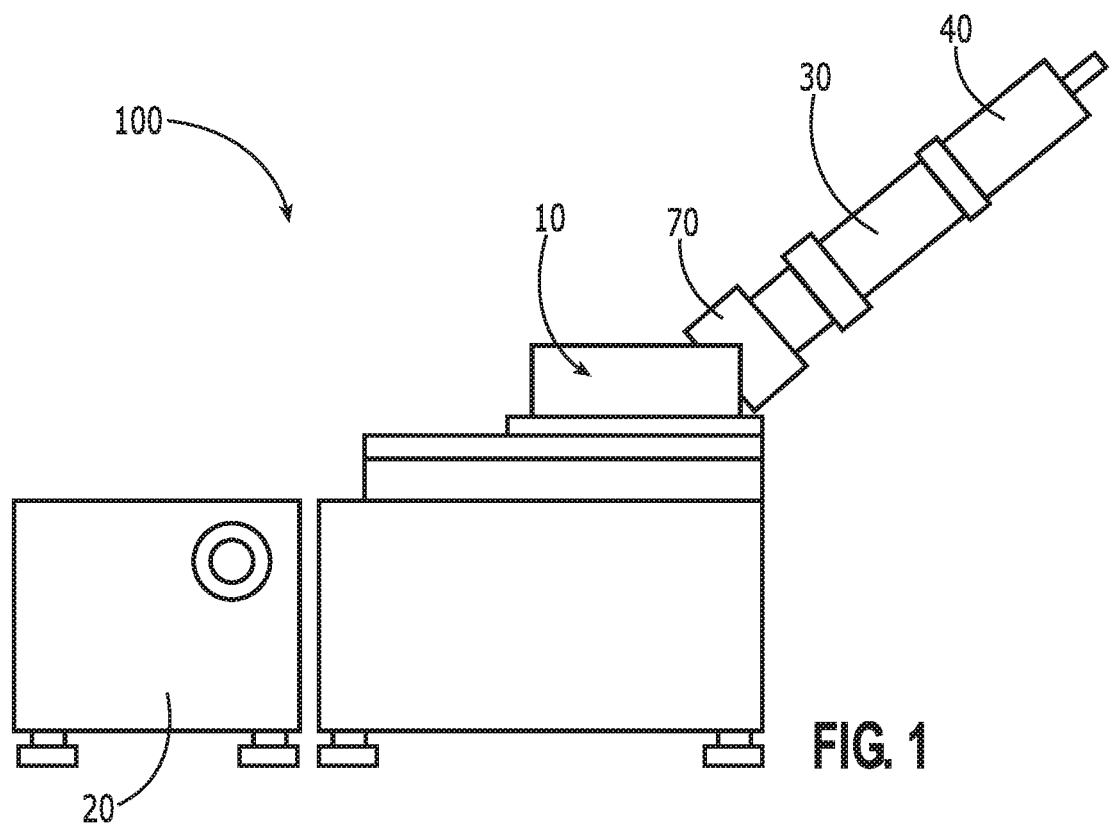
FIG. 1 depicts an exemplary embodiment of a gemstone optical assessment system including an optical unit, a gemstone evaluation unit.

Unless otherwise noted, terms are to be understood according to conventional usage by those of ordinary skill in the relevant art. For illustration purposes, diamonds are used as the representative gemstones. One of skill in the art would understand that the apparatuses, systems and methods disclosed herein are applicable to all types of gemstones capable of emitting fluorescence upon UV exposure. Systems and methods for fluorescence grading based on similar apparatuses are disclosed in U.S. patent application Ser. No. 14/673,780, filed on Mar. 30, 2015, and entitled "APPARATUS AND METHOD FOR ASSESSING FLUORESCENCE GRADING OF GEMSTONES" and filed concurrently herewith, which is hereby incorporated by reference herein in its entirety.

The currently available color grade instrument works quite well for color grading of certain type of gemstones; for example, regular round brilliant cut (RBC) diamond stones that are in the range of D-Z color grade of cape yellow hue. However, similar success is not observed for gemstones with irregular shapes, cut, sizes, or uncommon colors. In particular, the current instrument cannot provide consistent and reproducible color grade to brown stones, off-color stones (pink, yellowish-green, green and blue) and fancy shape cut stones (Step Cuts, Hearts, Marquises, Ovals, Pears, Triangles, Princess and other cuts rather than RBC).

Several critical issues are to be solved before better and more practical color grading instrument is built. For example, current instrument uses optical fiber to detect the light coming out of diamond. As a consequence, color grade is affected significantly by diamond position relative to the optical axis of fiber: getting reproducible results is difficult because the system set up requires that a test gemstone must be in exactly the same position. Further, color grade is significantly affected by the small change of distance between fiber edge and diamond and also the angle of optical fiber. This also leads to the inconsistent color grade among different devices since optical setup is extremely difficult and its alignment is easily changed during daily operation.

In order to overcome the existing issues, an improved color grade instrument as disclosed herein as the following characteristics: (1) to provide consistent and reproducible color grade to diamonds with different hue range (brown, pink, green and blue); (2) to provide consistent and reproducible color grade to any kinds of fancy shape diamonds; (3) to provide consistent and reproducible color grade with easy and quick operation (e.g., operators do not need to put stones in the same position); and (4) to be simple so that optical setup is easy and robust enough to daily operation.

In one aspect, provided herein is an improved color grading apparatus for color assessment of gemstones such as cut diamonds. The apparatus is suitable for grading any gemstones such as cut diamonds, including gemstones of irregular shapes, sizes and colors. For example, the apparatus can grade a gemstone with one or more curved edges, a gemstone with one or more straight edges, a gemstone with a combination of straight and curved edges, a gemstone with high or low depth, a stone with unusual shape such as marquise, emerald, and cushion, as well as a stone with unusual colors such as pink, blue, brown, green, yellow and etc. An exemplary apparatus 100 is illustrated in FIG. 1, which includes but is not limited to, for example, a gemstone evaluation component 10, a light source 20, a telecentric lens 30, and an image capturing component 40.

Based on functionality, the components of an apparatus disclosed herein can be divided into two main units: a gemstone presentation unit and an optical unit. The gemstone presentation unit provides uniform illumination to gemstones being analyzed and the optical unit captures images of gemstones being presented.

Additionally and not depicted in FIG. 1, an exemplary apparatus further comprises a computer processing unit for analyzing information collected by the image capturing component.

Figure 2A:
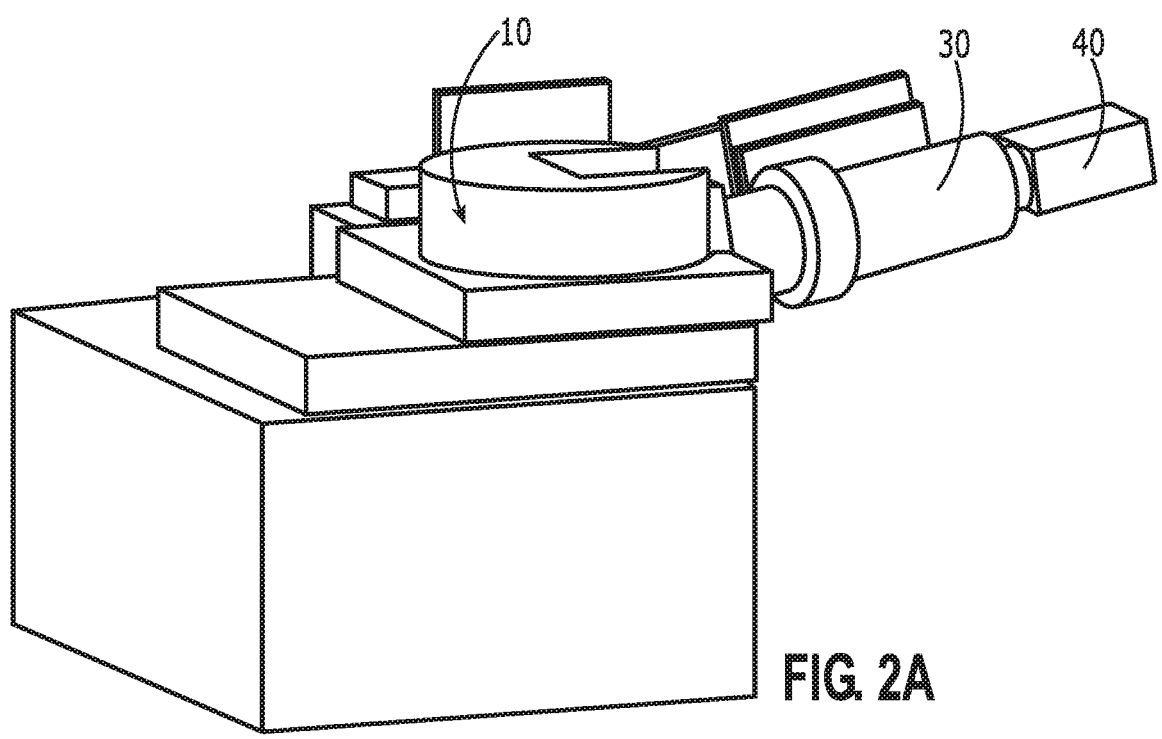
FIG. 2A depicts an exemplary schematic embodiment of a gemstone optical assessment system in a closed configuration.
Figure 2B:
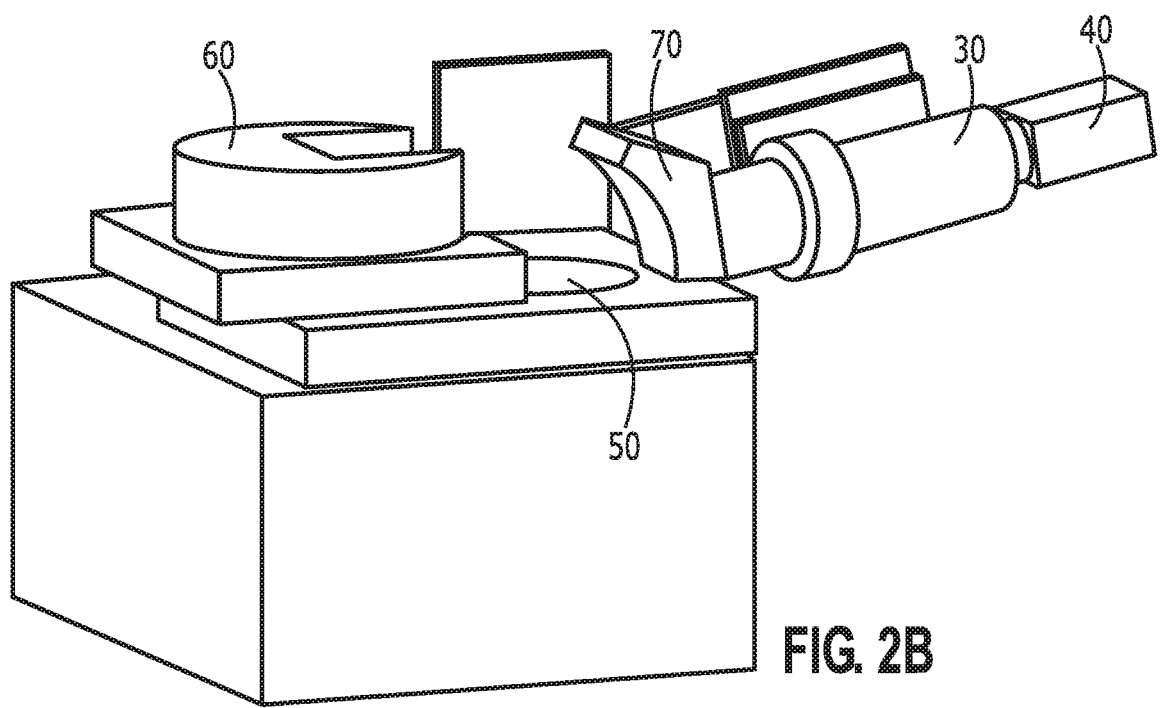
FIG. 2B depicts an exemplary schematic embodiment of a gemstone optical assessment system in an opened configuration.

As illustrated in FIG. 1, an exemplary gemstone presentation unit in turn comprises at least two parts: gemstone evaluation component 10 and a light source 20. The gemstone evaluation component is where a gemstone is presented. As depicted in FIGS. 2A and 2B, the gemstone evaluation component has a closed and an open configuration. In the closed configuration (see, e.g., FIG. 2A), a gemstone subject to analysis is completely concealed and not visible from an observer. In some embodiments, in order to avoid the inconsistencies caused by interference from other light such as ambient light, gemstone evaluation component is isolated and closed system from which ambient light or other light is excluded. The gemstone evaluation component and optic unit are joined in a complementary manner such that ambient light or other light is excluded from a concealed sample chamber within which a sample gemstone is housed.

Under the closed configuration, image information concerning the gemstone being analyzed is received and captured by the optical unit, which comprises a telecentric lens 30 and an image capturing device 40 (e.g., a camera).

In the open configuration (see, e.g., FIG. 2B), no image information is collected. Instead, the gemstone subject to analysis is exposed to an observer. In the open configuration, the gemstone presentation unit is revealed to have two parts: a bottom presentation component 50 and a top reflector component 60. In some embodiments, as illustrated in FIG. 2B, the top reflector component is mounted on movable side tracks. When the top reflector is moved on these tracks away from the optical unit, the bottom presentation component 50 is exposed. As shown in FIG. 2B, the shape and design of the opening of the top reflector component 60 is complementary to the shape and design of the optical connector module (e.g., element 70 in FIG. 2B) of the optical unit. In some embodiments, the optical connector module is a lens hood to which the telecentric lens 30 is attached.

Figure 3:
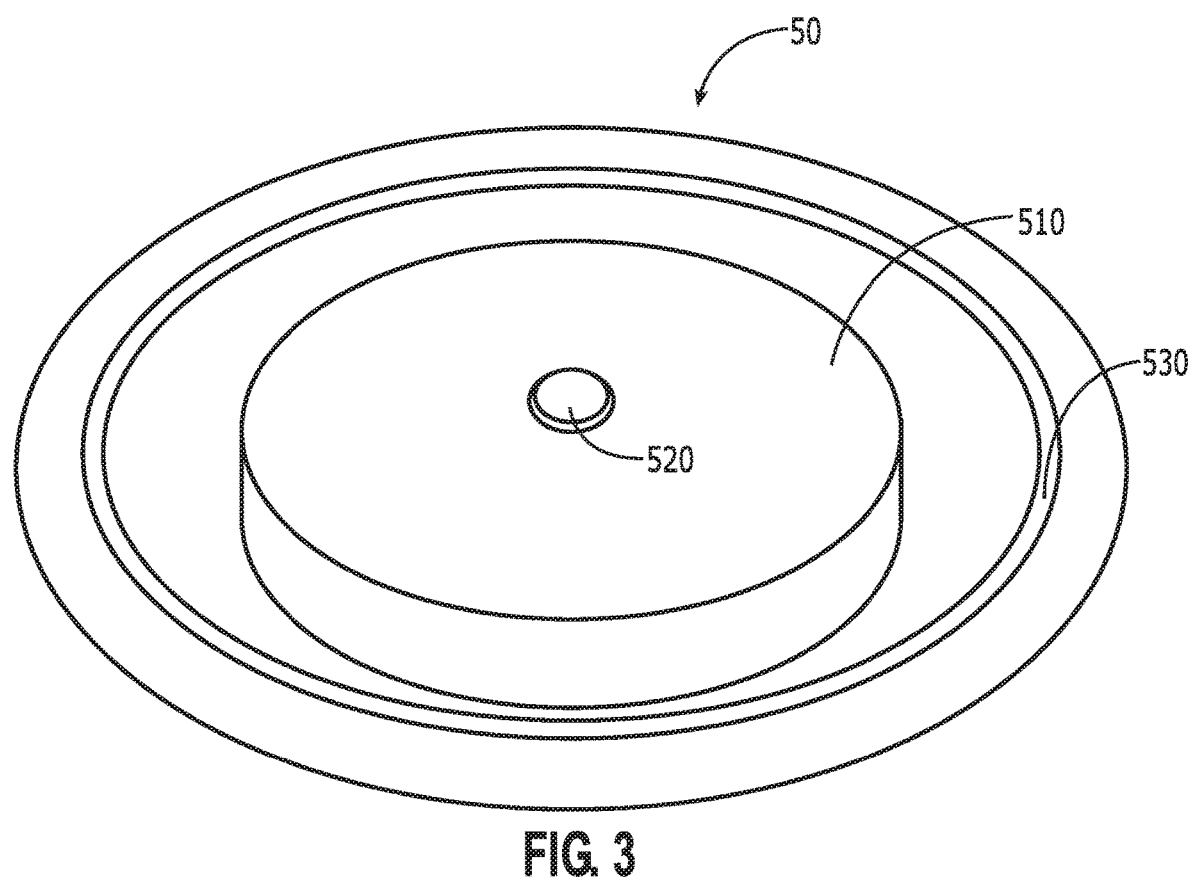
FIG. 3 depicts an exemplary embodiment of a sample platform with surrounding ring light illumination.

An exemplary bottom presentation component 50 is illustrated in FIG. 3. A circular white reflective platform 510 functions as the base on which a sample gemstone 520 is placed. A concentric circular ring light 530 is placed outside the circular platform such that the platform is completely enclosed within ring light 530.

Platform 510, also referred to as a stage or sample stage, is critical for the system disclosed herein. Importantly, it provides support to a gemstone that is being analyzed. In some embodiments, the top surface of the platform is a horizontal and flat. In addition, it functions as a stage for data collection by telecentric lens 30 and image capturing device 40 and subsequent analysis. In order to achieve data consistency, telecentric lens 30 is positioned at a first pre-determined angle relative to the top surface of platform 510. In some embodiments, image capturing device 40 is positioned at positioned at a second pre-determined angle relative to the top surface of platform 510. In some embodiments, the first and second pre-determined angles are the same and it has been optimized for data collection. In some embodiments, the first and second pre-determined angles are different, but each has been optimized for data collection. The first and second pre-determined angles can be referred to as the image or camera view angle.

Figure 4:
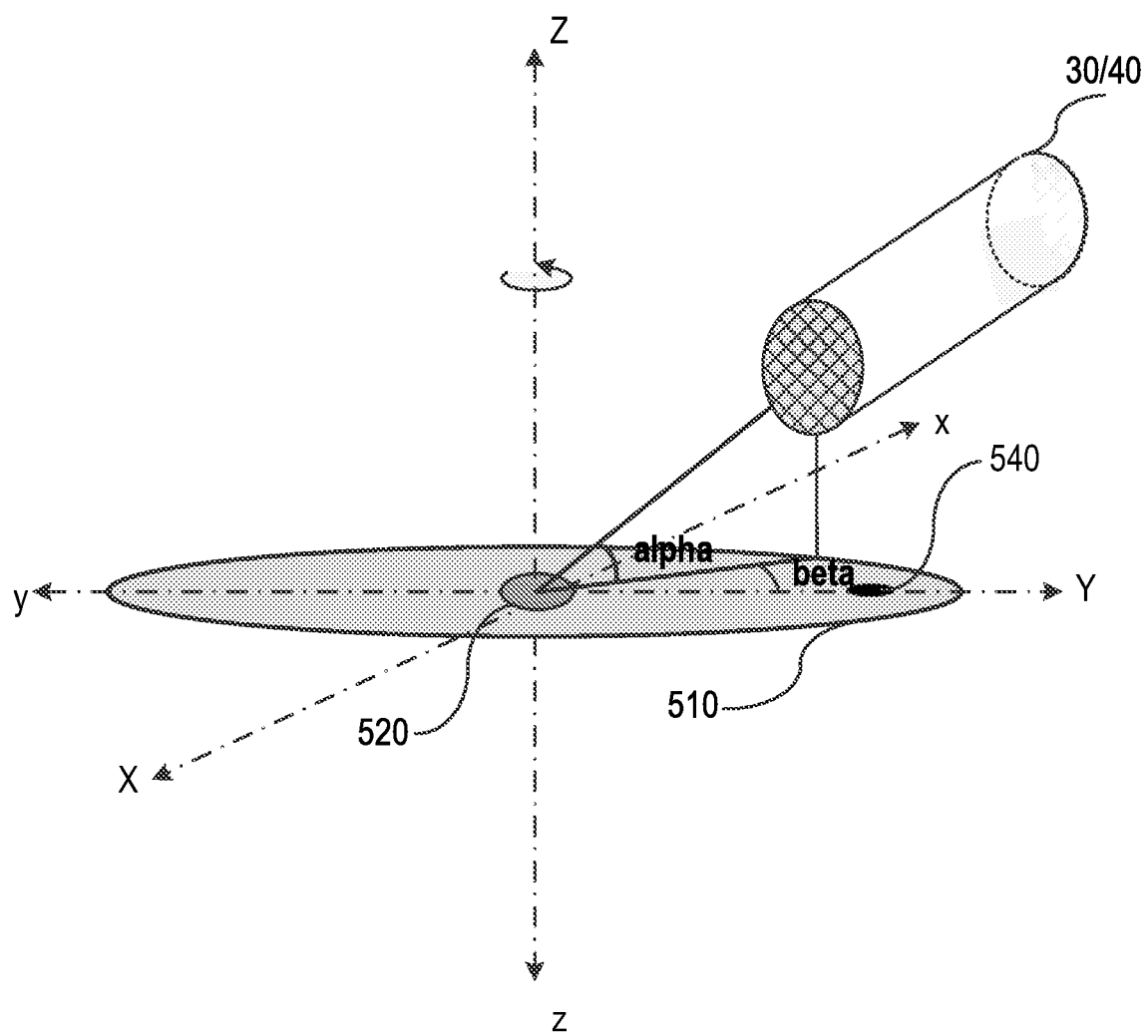
FIG. 4 depicts an exemplary schematic illustrating image view angle and image rotational angle.
Figure 5A:
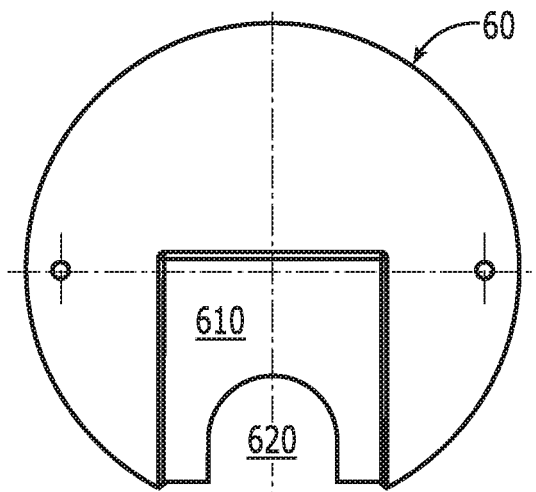
FIG. 5A depicts an exemplary embodiment of a top reflector with internal reflective surface.
Figure 5B:
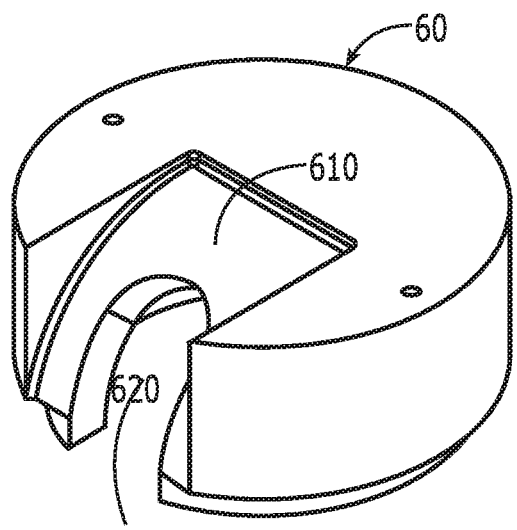
FIG. 5B depicts an exemplary embodiment of a top reflector with internal reflective surface.
Figure 5C:
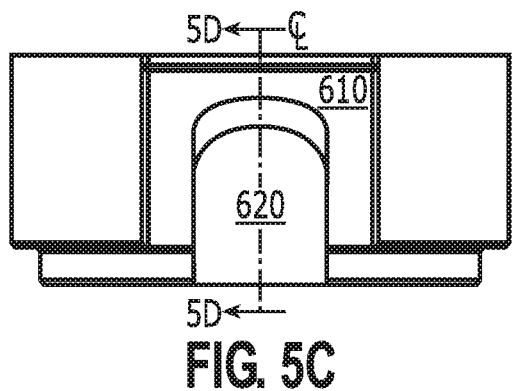
FIG. 5C depicts an exemplary embodiment of a top reflector with internal reflective surface.
Figure 5D:
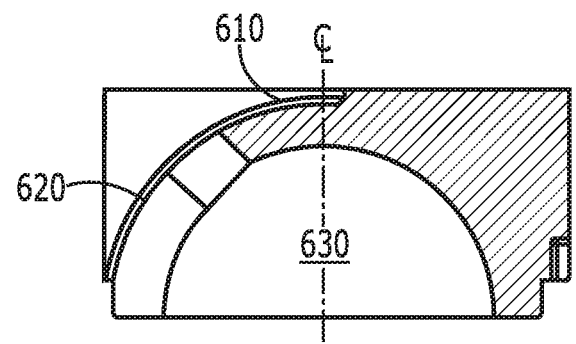
FIG. 5D depicts an exemplary embodiment of a top reflector with internal reflective surface.

An exemplary illustration of the relative configuration of the top surface of platform 510 to the optical unit (e.g., telecentric lens 30 and camera 40) is depicted in FIG. 4. Here, the optical unit, including both telecentric lens 30 and image capturing device 40, is positioned at a pre-determined angle (alpha) relative to the platform surface.

In some embodiments, the circular reflective platform is rotatable. For example, the platform is mounted on or connected with a rotor. In preferred embodiments, a gemstone being subjected to analysis is placed at the center of the platform surface, as illustrated in FIG. 3. The platform is then rotated in relation to the optical unit such that images of the gemstone at different angles are collected by the image capturing device.

In some embodiment, the platform surface is rotated around a rotational axis that goes through the center of origin of the circular platform surface and is perpendicular to the platform surface; see, for example, axis Zz depicted in FIG. 4.

In some embodiments, the platform is rotated in relation to the optical unit at set angular variations. The magnitude of the angular variations determines the extent of data collection; for example, how many images will be collection of the gemstone. For example, if the platform is rotated at an angular variation of 12 degree, a full rotation will allow 30 images of the gemstone to be collected. The angular variation can be set at any value to facilitate data collection and analysis. For example, the platform can be rotated at an angular variation of 0.5 degree or smaller, 1 degree or smaller, 1.5 degree or smaller, 2 degree or smaller, 3 degree or smaller, 4 degree or smaller, 5 degree or smaller, 6 degree or smaller, 7 degree or smaller, 8 degree or smaller, 9 degree or smaller, 10 degree or smaller, 12 degree or smaller, 15 degree or smaller, 18 degree or smaller, 20 degree or smaller, 24 degree or smaller, 30 degree or smaller, 45 degree or smaller, 60 degree or smaller, 90 degree or smaller, 120 degree or smaller, 150 degree or smaller, or 180 degree or smaller. It will be understood that the angular rotational variation can be set at any number. It will also be understood that the platform can be rotated for a total rotational angle of any value, not limited to a 360 degree full rotation. In some embodiments, data (e.g., color images) are collection for a rotation less than a 360 degree full rotation. In some embodiments, data (e.g., color images) are collection for a rotation more than a 360 degree full rotation.

In some embodiments, the platform or a portion thereof (e.g., the top surface) is coated with a reflective surface to achieve reflectivity. In some embodiments, the platform or a portion thereof (e.g., the top surface) comprises a reflective material. In some embodiments, the platform or a portion thereof (e.g., the top surface) is made of a reflective material. In some embodiments, the reflective material is a white reflective material. In some embodiments, the reflective material is Teflon™ material. In some embodiments, the reflective material includes but is not limited to polytetrafluoroethylene (PTFE), Spectralon™, barium sulfate, Gold, Magnesium Oxide, or combinations thereof.

Preferably, the rotatable platform is round and larger than the size of any sample gemstone to be analyzed. In some embodiments, the platform is horizontal and remains horizontal while it is being rotated.

In some embodiments, the height of the platform is fixed. In some embodiments, the height of the platform is adjusted, either manually or via the control of a computer program. Preferably, the platform can be raised or lowered by via the control of a computer program run by the computer unit.

In some embodiments, the platform is flat. In some embodiments, the center area on which the gemstone sample is positioned is flat and the more peripheral area on the platform is not flat. The entire platform adopts the confirmation of a flatted dome-like structure.

In some embodiments, the relative position between the platform and the illumination source can be adjusted. For example, the illumination source can be moved closer or further away from the platform.

A platform can be made of any rigid and non-transparent material such as metal, wood, dark glass, plastic or other rigid polymeric material. In some embodiments, the platform and/or area surrounding the platform are coated with non-reflective or low-reflective material.

In the broadest sense, a light source 20 includes but is not limited to the source for generating light, one or more filters, elements for conducting the generated light, and a component (e.g., a circular ring light) that emit the light as illumination. As disclosed herein, the source for generating light is sometimes referred to as light source. One of skill in the art would understand that the illumination component is also a part of the light source.

In some embodiments, the light generating source is separated from the ultimate illumination component, for example, it is connected with a circular ring light (e.g., by light transmission cables) to provide the source of illumination. In some embodiments, the light generating source itself is the circular ring light. Here, elements that can generate illumination is arranged into a circular or near circular shape. In the embodiment depicted in FIG. 3, a circular ring light 530 provides illumination to the sample gemstone.

In preferred embodiments, the light source is a daylight-approximating light source. Exemplary daylight-approximating light source includes but is not limited to one or more halogen lamps with a color balancing filter, multiple light emitting diodes arranged in a ring-like structure surrounding the platform surface, fluorescence lamp, Xe lamp, Tungsten lamp, metal halide lamp, laser-induced white light (LDLS), or combinations thereof.

In some embodiments, cables such as gooseneck light guide, flexible light guide, each containing one or more branches are used to connected the ring light with the light source.

The illumination source can adopt any shape and size that are suitable for the optical analysis of a sample gemstone. For example, the illumination source can be a point light, a round light, a ring light, an oval light, a triangular light, a square light, or any other light with suitable size and shape. In some embodiments, the light illuminating source is ring-like or circular in shape, with a diameter that is larger than that of a circular platform.

In some embodiments, the circular ring light is equipped with one or more light source. For example, the ring light can be a circular fluorescent light bulb. In some embodiments, the ring light has embedded within one or more light emitting diodes (LEDs). In such embodiments, light source and circular ring lights can be used interchangeably. In some embodiments, a light source is positioned above a gemstone; for example, a lamp or one or more LEDs are placed above the platform. The gemstone subject to analysis is irradiated via an optical diffuser as described in U.S. Pat. No. 6,473,164, which is hereby incorporated by reference herein in its entirety.

An illumination component provides the input light under which the sample gemstone can be analyzed. In some embodiments a form of illumination is chosen that it is a reasonably good approximation to the theoretical CIE standard illuminant D65.

A modular approach to the design of the apparatus has been adopted to provide experimental flexibility. This also applies to the ways in which gemstones such diamonds are illuminated. For stones mounted table-down, two illumination configurations have been used: from the rear and from overhead.

In some embodiments, in order for light rays to contain information about the color of a diamond, they must have passed through the stone. No color information is contained in rays that are reflected off the front facets of the diamond. At first sight, therefore, it would appear sensible to provide illumination substantially from the rear of the diamond while avoiding illuminating the front of the diamond.

In some embodiments, the uneven brightness of the image can be avoided if the diffuse illumination comes from above the diamond and from a much larger range of azimuthal angles. Top illumination has the advantage of much more closely emulating the illumination geometry used in visual grading but, of course, includes front-surface reflections.

In order to achieve this top illumination geometry, a new illuminator base plate was manufactured to accommodate a fiber-optic annular "ring-light." Preferably, the diameter of the fiber-optic ring light is larger than the diameter of the platform upon which the gemstone is placed. For example, the diameter of a fiber-optic ring light is 10 mm or larger, 16 mm or larger, 20 mm or larger, 24 mm or larger, 28 mm or larger, 32 mm or larger, 40 mm or larger, 44 mm or larger, 50 mm or larger, 56 mm or larger, 60 mm or larger, 64 mm or larger, 70 mm or larger, 80 mm or larger, 90 mm or larger, or 100 mm or larger. One of skill in the art would understand that the diameter of the ring light can be adjusted to optimize measurements of a particular gemstone sample. In some embodiments, the diameter of a fiber-optic ring light is 58 mm.

In some embodiments, the light source is positioned at the platform surface level or slightly below. In some embodiments, the light source is positioned above the platform surface. In some embodiments, the intensity of an illumination source can be adjusted to optimize image collection.

As shown in FIGS. 2A and 2B, a top reflector module can be moved over the area where a sample gemstone is positioned. In the closed configuration shown in FIG. 2A, the internal cavity of the top reflector module functions as a sealed and isolated sample chamber in which the sample gemstone is analyzed in a controlled environment. For example, ambient light or other light is excluded from the chamber. A user can adjust light intensity within the chamber to optimize data collection. In some embodiments, data collected include color images of the gemstone viewed from different angles.

FIGS. 5A through 5D illustrate an exemplary embodiment of the top reflector component 60. Overall, the top reflector has an external morphology that resembles that of a short cylinder, except that a portion of the cylinder is carved away to form a curved slope (see, for example, element 610 in FIGS. 5B and 5D). A portion of the slope is removed to allow access to the inside of the reflector component. For example, as shown in FIGS. 5A-5D, the lower portion of slope 610 is removed to form an opening 620. In some embodiments, the top port of opening 620 is circular in design; for example with a diameter through which a lens from the optical unit is fitted. In some embodiments, the diameter is the same as that of the telecentric lens to prevent ambient light or other light from entering the inside of the reflector. In some embodiments, the diameter is slightly larger than that of the telecentric lens such that an adaptor module is needed to prevent ambient light or other light from entering the inside of the reflector.

Inside of top reflector module 60 is reflective surface 630. This internal reflective surface is at least partially hemispherical. In some embodiments, the internal reflective surface adopts a shape that is part of the involute of a circle having a radius R. In preferred embodiments, the circle is located at the center of the platform surface and has a diameter that is larger than the sizes of the gemstones being analyzed. The shape of the involute surface is described based on the following equations:

$$x = R(\cos \theta + \theta \sin \theta)$$

$$y = R(\sin \theta - \theta \cos \theta),$$

where R is the radius of the circle and $\theta$ is an angle parameter in radians. The involute surface will reflect light toward the center circular region such that illumination of the gemstone being analyzed is optimized.

In some embodiments, the reflective surface 630 or a portion thereof comprises a reflective material. In some embodiments, the reflective surface 630 or a portion thereof is made of a reflective material. In some embodiments, the reflective material is a white reflective material. In some embodiments, the reflective material is Teflon™ material. In some embodiments, the reflective material includes but is not limited to polytetrafluoroethylene (PTFE), Spectralon™, barium sulfate, Gold, Magnesium Oxide, or combinations thereof. Additional reflective coating materials include but are not limited to a zinc salt (zinc sulfide), titanium dioxide, silicon dioxide, a magnesium salt (magnesium fluoride, magnesium sulfide).

As illustrated in FIG. 2B, an optical connector module 70 links the gemstone evaluation unit with the optical unit to permit data collection by image capturing device 40, whiling at the same time preventing ambient light or other light from entering the gemstone evaluation unit and interfering with data measurements.

Figure 6A:
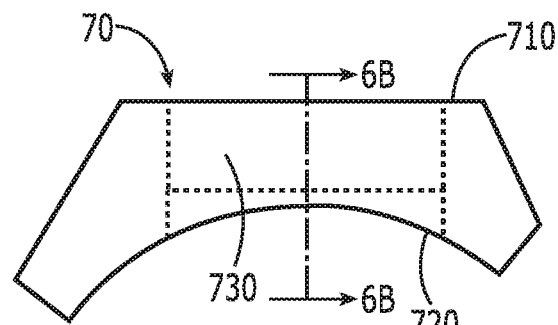
FIG. 6A depicts an exemplary embodiment of a connector module for linking a gemstone evaluation unit and an optic unit.
Figure 6B:
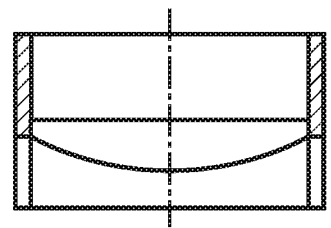
FIG. 6B depicts an exemplary embodiment of a connector module for linking a gemstone evaluation unit and an optic unit.
Figure 6C:
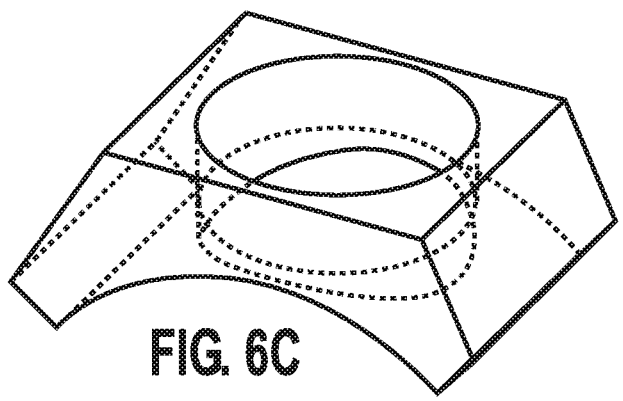
FIG. 6C depicts an exemplary embodiment of a connector module for linking a gemstone evaluation unit and an optic unit.

FIGS. 6A to 6C provide more detailed illustrations of an exemplary embodiment of an optical connector module. In this case, the connector is a lens hood for receiving the telecentric lens 30. On the side in contact with the telecentric lens, the lens hood has a flat surface 710. On the opposite side which contacts the reflector, the lens hood has a curved internal surface 720. In some embodiments, the curved surface 720 has a shape complementary to the curved surface 610 on the reflector.

Additionally, the connector also has an opening 730; see, FIGS. 6A, 6B, and 6C. In some embodiments, opening 730 has a configuration that accommodates the telecentric lens while preventing interference from ambient light or other light.

In some embodiments, internal surface 720 or a portion thereof comprises a reflective material. In some embodiments, internal surface 720 or a portion thereof is made of a reflective material. In some embodiments, the reflective material is a white reflective material. In some embodiments, the reflective material is Teflon™ material. In some embodiments, the reflective material includes but is not limited to polytetrafluoroethylene (PTFE), Spectralon™ barium sulfate, Gold, Magnesium Oxide, or combinations thereof. Additional reflective coating materials include but are not limited to a zinc salt (zinc sulfide), titanium dioxide, silicon dioxide, a magnesium salt (magnesium fluoride, magnesium sulfide).

A lens hood or other optical connector module allows integration of two different functional components. It is designed such that no or very little ambient light or other light enters the sample chamber. In some embodiments, additional elements such as a sealing tape can be used to exclude ambient light or other light.

Another main functional component of the system is an optical unit through which data of the gemstones being analyzed. The optical unit provides a sample chamber that enables the collection of a visible-light spectrum from an area containing a sample gemstone while excluding light from outside the chamber. Optical measurement such as an image is captured of the area containing the sample gemstone and, possibly through analysis of the detailed structure of the images, to provide some insight into the reasons for certain stones that previously had anomalous grading results.

Exemplary embodiments disclosed herein include but are not limited to two important functional modules in the optical unit a telecentric lens 30 and an image capturing component 40 such as a color camera. One of skill in the art would understand that additional components can be present to facilitate data collection.

A telecentric lens is used to provide an image of the illuminated gemstone to the image capturing component. Telecentricity refers to a unique optical property where the chief rays (oblique rays which pass through the center of the aperture stop) through a certain lens design are collimated and parallel to the optical axis in image and/or object space. A telecentric lens is a compound lens which has its entrance or exit pupil at infinity. Advantageously, a telecentric lens provides constant magnification (object size does not change) over a range of working distances, virtually eliminating perspective angle error. For many applications, this means that object movement does not affect image magnification, allowing for highly accurate measurements in gauging applications. This level of accuracy and repeatability cannot be obtained with standard lenses. The simplest way to make a lens telecentric is to put the aperture stop at one of the lens's focal points.

There are three types of telecentric lens. An entrance pupil at infinity makes a lens object-space telecentric. An exit pupil at infinity makes the lens image-space telecentric. If both pupils are at infinity, the lens is double telecentric.

Telecentric lens with high depth of field are used in the system disclosed herein. In some embodiments, a telecentric lens used is an object-space telecentric lens. In some embodiments, a telecentric lens is a double telecentric lens. In preferred embodiments, zoom should be fixed for all images collection for a given gemstone stone to further ensure consistency.

Advantageously, the present apparatus and system do not require that the sample gemstone be placed at the center of the platform surface. In addition, a telecentric lens does not discriminate the size of the sample gemstones. The same telecentric lens can be used to collection images for a very small gemstone and a significantly larger gemstone.

The optical unit further comprises an image capture component or a detector such as a digital camera.

In some embodiments, image capturing component 40 comprises one or more photodiode arrays of a CCD (charge coupled device). In some embodiments, image capturing component 40 comprises one or more CMOS (complementary metal oxide semiconductor) image sensors. In some embodiments, image capturing component 40 comprises a combination of one or more photodiode arrays with CMOS sensors. In some embodiments, image capturing component 40 is a CCD digital camera, such as a color digital camera. When images from different color grading apparatuses are analyzed, more consistent results can be obtained if the apparatuses use the same type of detection methods; for example, all CCD arrays, all CMOS sensors, or the same combination of both types.

For more accurate analytical results, the resolution limit for the digital images collected is 600 pixel×400 pixel or above. In some embodiments, each pixel has an 8-bit value (e.g., 0 to 255) for each color component. The Analog to Digital Converter (ADC) of the digital camera is 8-bit or above in order to efficiently process the information embedded in the pixels without little or no loss of image quality. In some embodiments, the ADC is 10-bit or above according to the dynamic range of image capturing component. In some embodiments, the ADC is between 10-bit and 14-bit.

In some embodiments, the color components in a pixel include but not limited to red (R), green (G) and blue (B). In some embodiments, the color components in a pixel include but not limited to) cyan (C), magenta (M), yellow (Y), and key (black or B). In some embodiments, the color components in a pixel include but not limited to red (R), yellow (Y) and blue (B).

In some embodiments, a multi-band camera or hyper spectrum camera is used for capturing images. A multi-band camera is capable to detect light in the infrared (IR) and far-infrared (FIR) ranges in addition to that of the visible spectrum. For example, a multi spectral camera enables a user to better discriminate targets from both background and decoys by blending color images with information from the IR band. Images obtained from such a system penetrate darkness, camouflage, smoke and clutter better than either visible or IR images could alone.

A hyper spectrum camera, like other spectral imaging devices, collects and processes information from across the electromagnetic spectrum, but beyond the visible range. The goal of hyperspectral imaging is to obtain the spectrum for each pixel in the image of a scene. Much as the human eye sees visible light in three bands (red, green, and blue), spectral imaging divides the spectrum into many more bands. Hyperspectral imaging technique divides images into bands that can be extended beyond the visible range. In hyperspectral imaging, the recorded spectra have fine wavelength resolution and cover a wide range of wavelengths, allowing a user to find objects, identify material or detect process that are previously impossible when using regular imaging techniques.

In one aspect, imaging techniques are used to approximate or simulate the visual perception of human eyes. For example, in some cases, a spectrum function $f(x)$ is used to describe the perception (e.g., color perception) of human eyes. It is understood that human eyes are more receptive to light in certain wavelengths or wavelength ranges while being less receptive to other wavelengths or wavelength ranges. In practice, the effects can be approximated or simulated by using multiple filters to weaken or eliminate the non-receptive light. In some embodiments, multiple images are taken for each image view angle and image rotational angle, where each image is taken using a band-pass filter. This way, gemstone images with multiple spectrum regions can be obtained. These images are then combined to form a composite image that simulate the visual perception by human eyes. It will be understood that using only one band filter will unlikely match the effects described in spectrum function $f(x)$ and more band-filters will allow fine tuning and eventual close matching the described visual effects.

Image view angle: As depicted in FIG. 4, an image capturing device (or telecentric lens 30 or both) is positioned at a pre-determined angle (alpha, also referred to as the image view angle) relative to the platform surface. In some embodiments, the image view angle is 65 degree or smaller, 60 degree or smaller, 56 degree or smaller, 52 degree or smaller, 50 degree or smaller, 48 degree or smaller, 46 degree or smaller, 44 degree or smaller, 42 degree or smaller, 40 degree or smaller, 39 degree or smaller, 38 degree or smaller, 37 degree or smaller, 36 degree or smaller, 35 degree or smaller, 34 degree or smaller, 33 degree or smaller, 32 degree or smaller, 31 degree or smaller, 30 degree or smaller, 29 degree or smaller, 28 degree or smaller, 27 degree or smaller, 26 degree or smaller, 25 degree or smaller, 24 degree or smaller, 23 degree or smaller, 22 degree or smaller, 21 degree or smaller, 20 degree or smaller, 19 degree or smaller, 18 degree or smaller, 17 degree or smaller, 16 degree or smaller, 15 degree or smaller, 14 degree or smaller, 13 degree or smaller, 12 degree or smaller, 11 degree or smaller, or 10 degree or smaller. In some embodiments, the image view angle is between about 10 degree and about 45 degree. For consistency, the image view angle for a given gemstone will remain constant when images are collected.

Image rotational angle: Also as illustrated in FIG. 4, the relative rotational position between the imaging capturing component and a pre-defined location on the platform (e.g., point 540) can be described by an image rotational angle beta. For example, the image capturing component and the platform surface can be rotated relative to each other such that the image rotational angle is varied by a set angular variation between consecutive images. For example, the angular variation between two consecutive images can be 0.5 degree or smaller, 1 degree or smaller, 1.5 degree or smaller, 2 degree or smaller, 3 degree or smaller, 4 degree or smaller, 5 degree or smaller, 6 degree or smaller, 7 degree or smaller, 8 degree or smaller, 9 degree or smaller, 10 degree or smaller, 12 degree or smaller, 15 degree or smaller, 18 degree or smaller, 20 degree or smaller, 24 degree or smaller, 30 degree or smaller, 45 degree or smaller, 60 degree or smaller, 90 degree or smaller, or 180 degree or smaller. It will be understood that the angular rotational variation can be set at any number.

It will also be understood that the platform and image capturing component can be rotated relative to each other for a total rotational angle of any value, not limited to a 360 degree full rotation. In some embodiments, data (e.g., color images) are collection for a rotation less than a 360 degree full rotation. In some embodiments, data (e.g., color images) are collection for a rotation more than a 360 degree full rotation.

It is possible to change angular rotational variation when collecting a set of images for the same sample gemstone. For example, the angular different between image 1 and image 2 can be 5 degrees, but the different between image 2 and 3 can be 10 degrees. In preferred embodiments, angular difference between consecutive images remains constant within the same set of images for the same sample gemstone. In some embodiments, only one set of images is collection for a given sample gemstone. In some embodiments, multiple sets of images are collected for the same gemstone where angular differences remain constant within each set but are different from each other. For example, a first set of images is collected by varying the rational image angle by 12 degree for consecutive images, while a second set of images is collected by varying the rational image angle by 18 degree for consecutive images.

The number of images collected for a given sample gemstone varies depending on the characteristics of the gemstone. Exemplary characteristics include but are not limited to shape, cut, size, color and etc.

Visible-light spectra from an area on the platform surface that contains the sample gemstone is selectively collected. In some embodiments, multiple color images are collected for each gemstone. In some embodiments, multiple non-color images are collected for each gemstone. Color images are advantageous for determining, for example, the color grade of a cut diamond.

In some embodiments, the image capturing component or detector is a Nikon Digital Sight 5.0 megapixel color CCD camera head, DS-Fil. This has a high spatial resolution with a field of view of 2560×1920 pixels and a reasonably high acquisition rate of 12 frames per second. In some embodiments, alternative cameras with alternative resolution are used.

In some embodiments, the image capturing component or detector is a CCD camera that has same filter function as human eyes and also higher color resolution, such as Konica Minolta: CA-2500. In some embodiments, the detector measures photo-luminescence by using microcomputer control.

In some embodiments, as will be discussed further in sections that follow, images captured by the CCD camera will be processed in order to identify regions of differing intensity of color. Furthermore, colorimetric calculations can be performed on these different areas using the red, green and blue signals from the camera pixels. In some embodiment, such calculations will be sufficiently accurate to give a color grade. In some embodiment, such calculations will be sufficiently accurate to provide a color distribution across the diamond and the comparison of these color calculations with that obtained from the measured spectrum can help identify diamonds that are likely to give anomalous results.

In some embodiments, the color grade is determined based on color values computed from the entire sample gemstone. In some embodiments, the color grade is determined based on color values computed from selected area of the sample gemstone.

Resolution and capacity of a detector can be determined by the number and size of the pixel in the detector arrays. In general, the spatial resolution of the digital image is limited by the pixel size. Unfortunately while reducing pixel size improves spatial resolution this comes at the expense of signal to noise ratio (SNR or signal/noise ratio). In particular, signal-to-noise ratio is improved when the image sensor pixel size is increased or when the image sensor is cooled. At the same time, size of the image sensor is increased if image sensor resolution is kept the same. Detectors of higher quality (e.g., better digital cameras) have a large image sensor and a relatively large pixel size for good image quality.

In some embodiments, a detector of the present invention has a pixel size of 1 $\mu m^2$ or smaller; 2 $\mu m^2$ or smaller; 3 $\mu m^2$ or smaller; 4 $\mu m^2$ or smaller; 5 $\mu m^2$ or smaller; 6 $\mu m^2$ or smaller; 7 $\mu m^2$ or smaller; 8 $\mu m^2$ or smaller; 9 $\mu m^2$ or smaller; 10 $\mu m^2$ or smaller; 20 $\mu m^2$ or smaller; 30 $\mu m^2$ or smaller; 40 $\mu m^2$ or smaller; 50 $\mu m^2$ or smaller; 60 $\mu m^2$ or smaller; 70 $\mu m^2$ or smaller; 80 $\mu m^2$ or smaller; 90 $\mu m^2$ or smaller; 100 $\mu m^2$ or smaller; 200 $\mu m^2$ or smaller; 300 $\mu m^2$ or smaller; 400 $\mu m^2$ or smaller; 500 $\mu m^2$ or smaller; 600 $\mu m^2$ or smaller; 700 $\mu m^2$ or smaller; 800 $\mu m^2$ or smaller; 900 $\mu m^2$ or smaller; 1,000 $\mu m^2$ or smaller; 1,100 $\mu m^2$ or smaller; 1,200 $\mu m^2$ or smaller; 1,300 $\mu m^2$ or smaller; 1,400 $\mu m^2$ or smaller; 1,500 $\mu m^2$ or smaller; 1,600 $\mu m^2$ or smaller; 1,700 $\mu m^2$ or smaller; 1,800 $\mu m^2$ or smaller; 1,900 $\mu m^2$ or smaller; 2,000 $\mu m^2$ or smaller; 2,100 $\mu m^2$ or smaller; 2,200 $\mu m^2$ or smaller; 2,300 $\mu m^2$ or smaller; 2,400 $\mu m^2$ or smaller; 2,500 $\mu m^2$ or smaller; 2,600 $\mu m^2$ or smaller; 2,700 $\mu m^2$ or smaller; 2,800 $\mu m^2$ or smaller; 2,900 $\mu m^2$ or smaller; 3,000 $\mu m^2$ or smaller; 3,100 $\mu m^2$ or smaller; 3,200 $\mu m^2$ or smaller; 3,300 $\mu m^2$ or smaller; 3,400 $\mu m^2$ or smaller; 3,500 $\mu m^2$ or smaller; 3,600 $\mu m^2$ or smaller; 3,700 $\mu m^2$ or smaller; 3,800 $\mu m^2$ or smaller; 3,900 $\mu m^2$ or smaller; 4,000 $\mu m^2$ or smaller; 4,100 $\mu m^2$ or smaller; 4,200 $\mu m^2$ or smaller; 4,300 $\mu m^2$ or smaller; 4,400 $\mu m^2$ or smaller; 4,500 $\mu m^2$ or smaller; 4,600 $\mu m^2$ or smaller; 4,700 $\mu m^2$ or smaller; 4,800 $\mu m^2$ or smaller; 4,900 $\mu m^2$ or smaller; 5,000 $\mu m^2$ or smaller; 5,100 $\mu m^2$ or smaller; 5,200 $\mu m^2$ or smaller; 5,300 $\mu m^2$ or smaller; 5,400 $\mu m^2$ or smaller; 5,500 $\mu m^2$ or smaller; 5,600 $\mu m^2$ or smaller; 5,700 $\mu m^2$ or smaller; 5,800 $\mu m^2$ or smaller; 5,900 $\mu m^2$ or smaller; 6,000 $\mu m^2$ or smaller; 6,500 $\mu m^2$ or smaller; 7,000 $\mu m^2$ or smaller; 7,500 $\mu m^2$ or smaller; 8,000 $\mu m^2$ or smaller; 8,500 $\mu m^2$ or smaller; 9,000 $\mu m^2$ or smaller; or 10,000 $\mu m^2$ or smaller. In some embodiments, the pixel size is larger than 10,000 $\mu m^2$, for example, up to 20,000 $\mu m^2$, 50,000 $\mu m^2$, or 100,000 $\mu m^2$.

In some embodiments, exposure time to the detector can be adjusted to optimize image quality and to facilitate the determination of a grade for an optical quality of the gemstone, such as color or fluorescence. For example, the exposure time to a CCD detector can be 0.1 millisecond (ms) or longer, 0.2 ms or longer, 0.5 ms or longer, 0.8 ms or longer, 1.0 ms or longer, 1.5 ms or longer, 2.0 ms or longer, 2.5 ms or longer, 3.0 ms or longer, 3.5 ms or longer, 4.0 ms or longer, 4.5 ms or longer, 5.0 ms or longer, 5.5 ms or longer, 6.0 ms or longer, 6.5 ms or longer, 7.0 ms or longer, 7.5 ms or longer, 8.0 ms or longer, 8.5 ms or longer, 9.0 ms or longer, 9.5 ms or longer, 10.0 ms or longer, or 15.0 ms or longer. It is understood that the time of exposure can vary with respect to, for example, light source intensity.

Figure 7A:
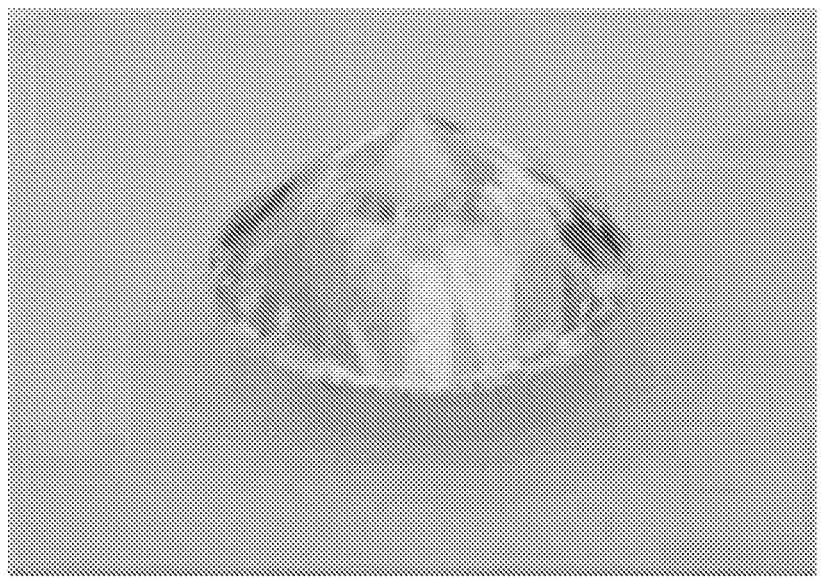
FIG. 7A depicts an exemplary embodiment before an outline mask is applied.
Figure 7B:
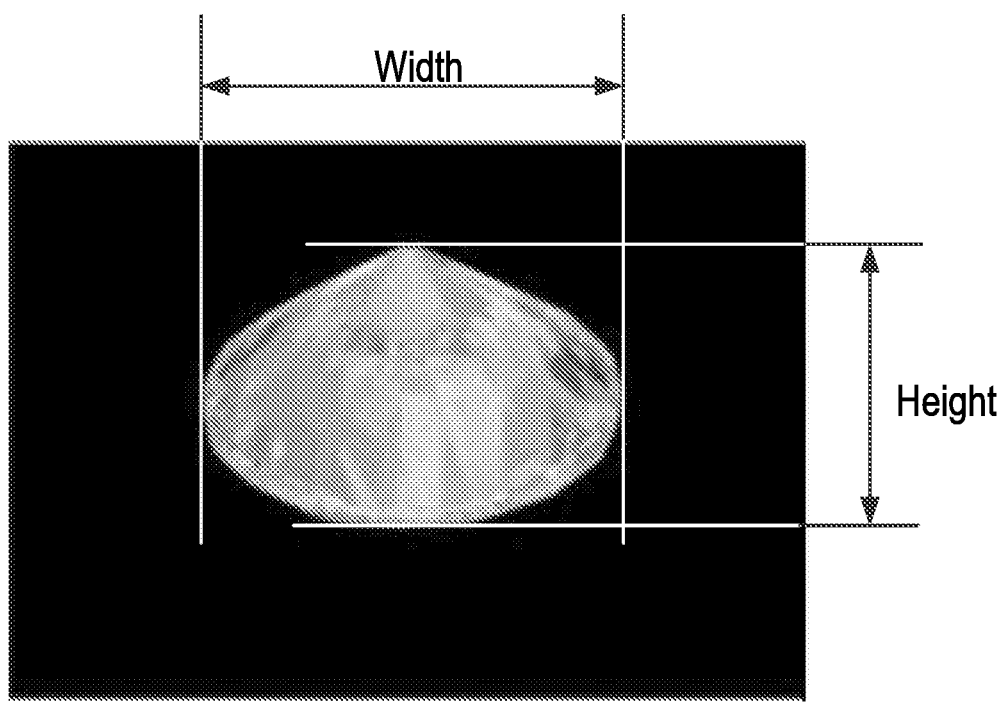
FIG. 7B depicts an exemplary embodiment after an outline mask is applied to highlight the width and height of a diamond.

FIGS. 7A and 7B illustrate images of a diamond in which the background white color has been masked by black color. The opening of this mask (an outline mask) corresponds to a full image of a diamond at a given image view angle and a given image rotational angle. As illustrated in the method of analysis section, such outline masks can be defined for each image to isolate the region of analysis and to extract measurements such as width and height.

In another aspect, also provided herein is a data analysis unit, including both a hardware component (e.g., computer) and a software component.

Figure 8:
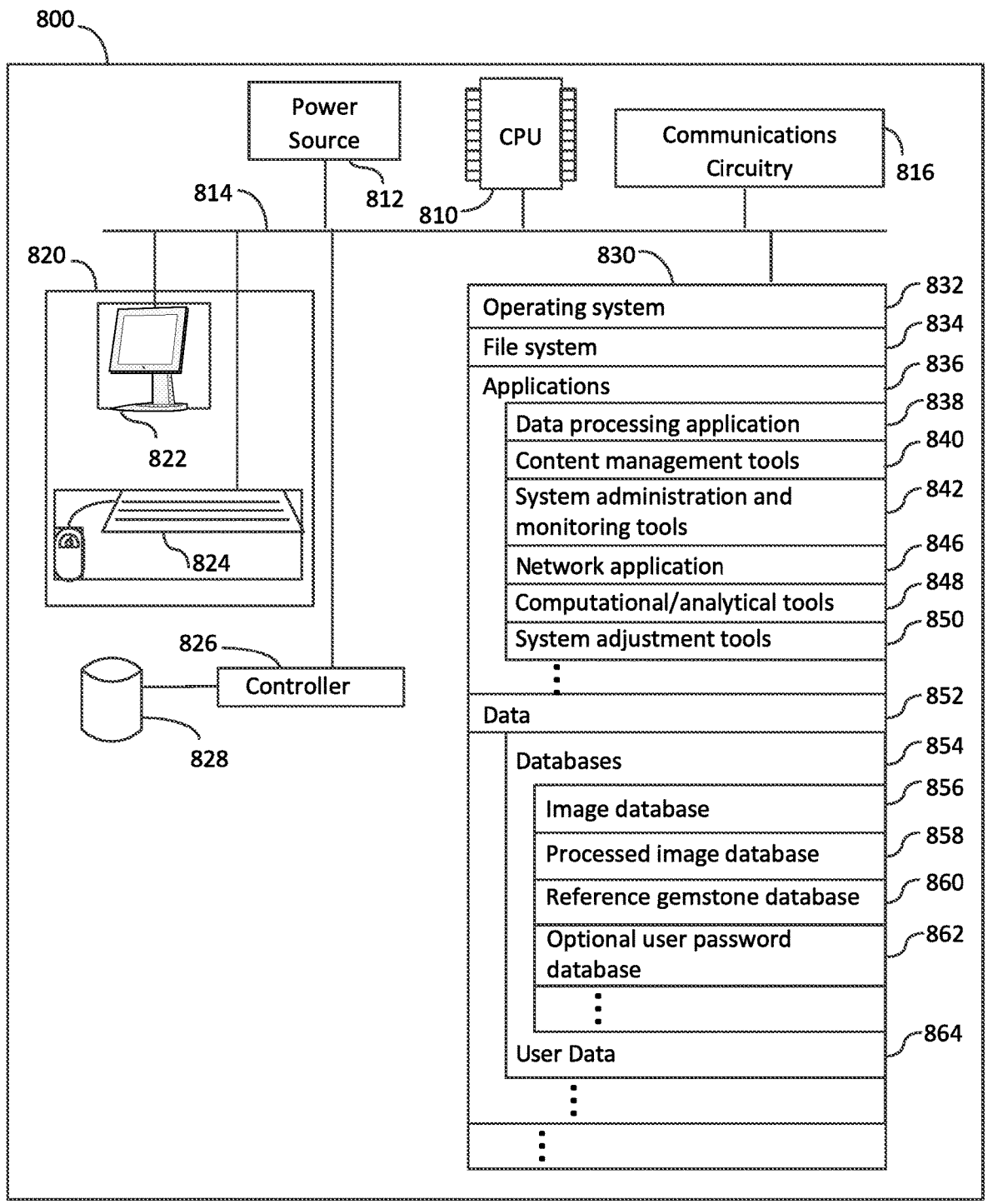
FIG. 8 depicts an exemplary organization of a computer system.

The data analysis unit stores, converts, analyzes, and processes of the images collected by the optical unit. The computer unit controls various components of the system, for example, rotation and height adjustment of the platform, adjustment of the intensity and exposure time of the illumination source. The computer unit also controls the zoom, adjusts relative position of the optic unit to the gemstone platform, FIG. 8 illustrates an exemplary computer unit 800. In some embodiments, a computer unit 800 comprises a central processing unit 810, a power source 812, a user interface 820, communications circuitry 816, a bus 814, a non-volatile storage controller 826, an optional non-volatile storage 828, and a memory 830.

Memory 830 may comprise volatile and non-volatile storage units, for example random-access memory (RAM), read-only memory (ROM), flash memory and the like. In some embodiments, memory 830 comprises high-speed RAM for storing system control programs, data, and application programs, e.g., programs and data loaded from non-volatile storage 828. It will be appreciated that at any given time, all or a portion of any of the modules or data structures in memory 830 can, in fact, be stored in memory 828.

User interface 820 may comprise one or more input devices 824, e.g., keyboard, key pad, mouse, scroll wheel, and the like, and a display 822 or other output device. A network interface card or other communication circuitry 816 may provide for connection to any wired or wireless communications network. Internal bus 814 provides for interconnection of the aforementioned elements of the computer unit 800.

In some embodiments, operation of computer unit 800 is controlled primarily by operating system 832, which is executed by central processing unit 810. Operating system 832 can be stored in system memory 830. In addition to operating system 832, a typical implementation of system memory 830 may include a file system 834 for controlling access to the various files and data structures used by the present invention, one or more application modules 836, and one or more databases or data modules 852.

In some embodiments in accordance with the present invention, applications modules 836 may comprise one or more of the following modules described below and illustrated in FIG. 8.

Data processing application 838: In some embodiments in accordance with the present invention, a data processing application 838 receives and processes optical measurements shared between the optical unit and data analysis unit. In some embodiments, data processing application 838 utilizes an algorithm to determine the portion of the image that corresponds to the sample gemstone and eliminates the irrelevant digital data (e.g., edge defining and mask application). In some embodiments, data processing application 838 converts each pixel of the digital images into individual color components.

Content management tools 840: In some embodiments, content management tools 840 are used to organize different forms of data 852 into multiple databases 854, e.g., an image database 856, a processed image database 858, a reference gemstone database 860, and an optional user password database 862. In some embodiments in accordance with the present invention, content management tools 840 are used to search and compare any of the databases hosted on computer unit 800. For example, images of the same sample gemstone taken at different time can be organized into the same database. In addition, information concerning the sample gemstone can be used to organize the image data. For example, images of diamonds of the same cut may be organized into the same database. In addition, images of diamonds of the same source may be organized into the same database.

The databases stored on the computer unit 800 comprise any form of data storage system including, but not limited to, a flat file, a relational database (SQL), and an on-line analytical processing (OLAP) database (MDX and/or variants thereof). In some specific embodiments, the databases are hierarchical OLAP cubes. In some embodiments, the databases each have a star schema that is not stored as a cube but has dimension tables that define hierarchy. Still further, in some embodiments, the databases have hierarchy that is not explicitly broken out in the underlying database or database schema (e.g., dimension tables are not hierarchically arranged).

In some embodiments, content management tools 840 utilize a clustering method for determining grading characteristics.

System administration and monitoring tools 842: In some embodiments in accordance with the present invention, the system administration and monitoring tools 842 administer and monitor all applications and data files of computer unit 800. System administration and monitoring tools 842 control which users, servers, or devices have access to computer unit 800. In some embodiments, security administration and monitoring is achieved by restricting data download or upload access from computer unit 800 such that the data is protected against malicious access. In some embodiments, system administration and monitoring tools 842 use more than one security measure to protect the data stored on computer unit 800. In some embodiments, a random rotational security system may be applied to safeguard the data stored on remote computer unit 800.

Network application 846: In some embodiments, network applications 846 connect computer unit 800 to network and thereby to any network devices. In some embodiments, a network application 846 receives data from intermediary gateway servers or one or more remote data servers before it transfers the data to other application modules such as data processing application 838, content management tools 840, and system administration and monitoring tools 842.

Computational and analytical tools 848: Computational and analytical tools 848 can apply any available methods or algorithm to analyze and process images collected from a sample gemstone.

System adjustment tools 850: System adjustment tools 850 controls and modifies configurations of various components of the system. For example, system adjustment tools 850 can switch between different masks, alter the size and shape of an adjustable mask, adjust zoom optics, set and modify exposure time, and etc.

Data module 852 and databases 854: In some embodiments, each of the data structures stored on computer unit 800 is a single data structure. In other embodiments, any or all such data structures may comprise a plurality of data structures (e.g., databases, files, and archives) that may or may not all be stored on computer unit 800. The one or more data modules 852 may include any number of databases 852 organized into different structures (or other forms of data structures) by content management tools 840.

In addition to the above-identified modules, various database 854 may be stored on computer unit 800 or a remote data server that is addressable by computer unit 800 (e.g., any remote data server that the computer unit can send information to and/or retrieve information from). Exemplary databases 854 include but are not limited to image database 856, processed image database 858, reference gemstone database 860, optional member password dataset 862, and gemstone data 864.

Image database 856 is used to store images of gemstones before they are analyzed. Processed image database 858 is used to store processed gemstone images. In some embodiments, processed image database 858 also stored data that are converted from processed images. Examples of converted data include but are not limited to individual color components of pixels in an image, a two or three dimensional map representing color distribution of the pixels in an image; computed $L^*$, $C^*$, a or b values of pixels in an image; average of $L^*$, $C^*$, a or b values for one or more images.

Reference gemstone database 860: Data of existing or known reference, or master gemstones (e.g., grade values or $L^*$, $C^*$, h values) are stored in reference gemstone database 860. In some embodiments, information of the known reference, or master gemstones is used as standards for determining the grade values, or $L^*$, $C^*$, h values of an unknown gemstone samples. The optical quality, such as color or fluorescence grade, has already been determined for the known reference, or master gemstones. For example, optical measurements of a sample diamond of brilliant cut are used to compute a value of $L^*$, $C^*$, h, which is then compared with the values of $L^*$, $C^*$, h of a plurality of known reference, or master diamond of the same cut. The grade of the sample diamond will be determined by comparing their $L^*$, $C^*$ and h with those of reference stones. In preferred embodiments, the reference gemstones are of the same or similar size or weight as the sample gemstone.

Optional user password database 862: In some embodiments, an optional password database 862 is provided. Password and other security information relating to users of the present system can be created and stored on computer unit 800 where passwords of the users are stored and managed. In some embodiments, users are given the opportunity to choose security settings.

In one aspect, provided herein are methods for system calibration, data collection, data processing and analysis. For example, color digital images of gemstones are processed and computed to render one or more values for assessing and grading quality of cut gemstones such as diamonds.

Figure 9A:
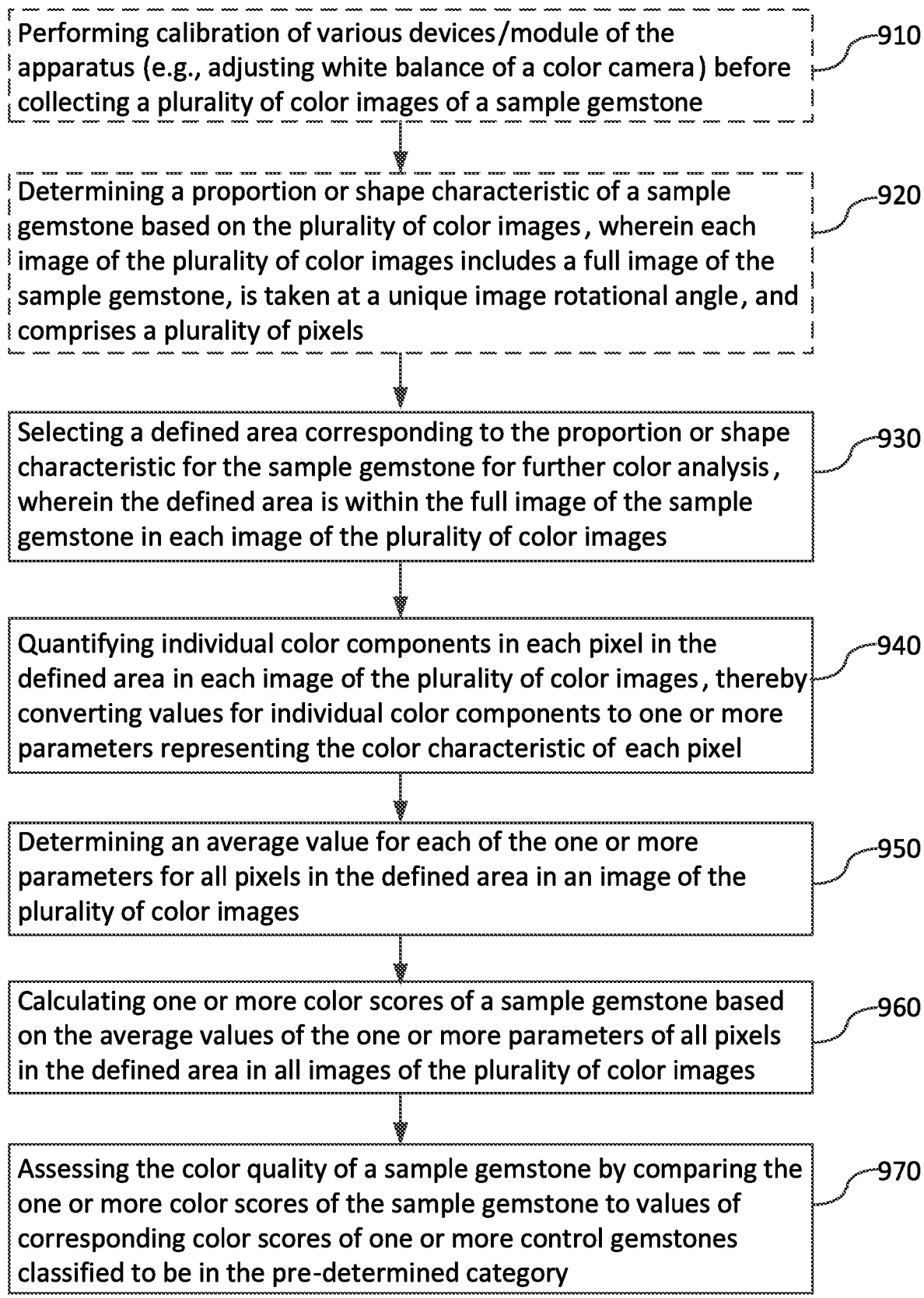
FIG. 9A depicts an exemplary process for a data collection and analysis.

An exemplary process based on the apparatus and system disclosed herein is outlined in FIG. 9A. One of skill in the art would understand the steps provided are exemplary and can be applied in any order or used in any possible combination.

At step 910, system calibration is performed. For example, in order to have reproducible results and cancel out the fluctuation of light source, white balance of an image capture component such as a color camera is adjusted. At this step, the pixel gains of individual color components (e.g., RGB) are adjusted such that the background image of the platform surface becomes white. Background adjustment is done with a bare platform surface; i.e., the sample gemstone is not yet positioned on the platform surface. Preferably, the background adjustment is done after the light source has stabilized. In some embodiments, the background adjustment is done with a short time period before images of a sample gemstone are collected. In some embodiments, the background adjustment is done after the light source has stabilized and soon before gemstone image collection. White background adjustment is performed when the top reflector module 60 is in closed configuration. The top reflector module is then opened and a user can place a sample gemstone at the center of the platform surface. Care is taken such that the platform surface, illumination and other conditions and settings in the sample chamber and for the optical unit remain the same before and after the sample gemstone is placed.

At step 920, a proportion or shape characteristic is determined based on a plurality of color images of the same sample gemstone. Here, each image includes a full image of the sample gemstone. Each image is taken at a unique image rotational angle and comprises a plurality of pixels. In some embodiments, the step of determining the proportion or shape characteristic is optional. For example, if by visual inspection, the sample gemstone has a perfect cut (e.g., a perfect round brilliant cut or RBC), there may be no need to determine the proportion or shape characteristic. A user can directly proceed to subsequent analysis.

Figure 9B:
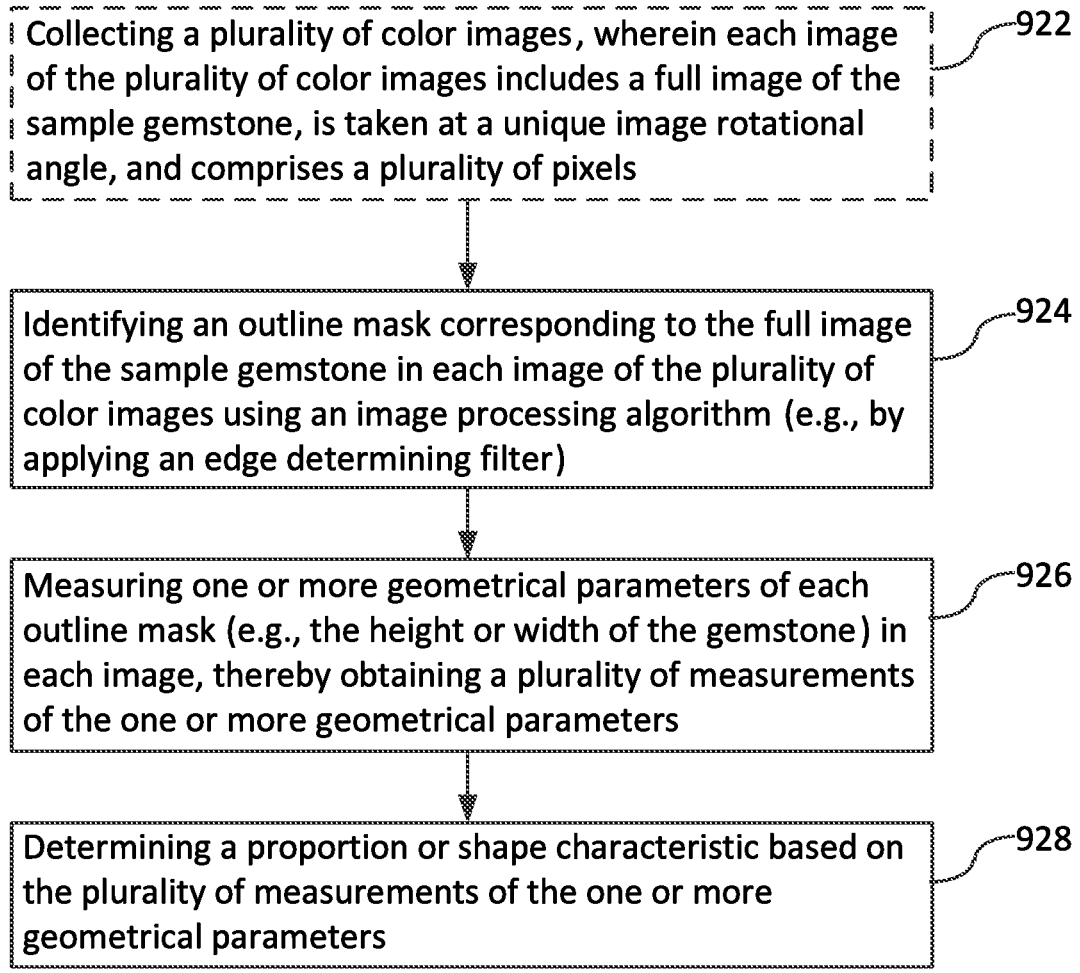
FIG. 9B depicts an exemplary process for a data collection and analysis.

A detailed exemplary process for determining the proportion or shape characteristic is outlined in FIG. 9B. First, the plurality of color images is collected at step 922. After the background adjustment is completed, a sample gemstone is placed on the platform surface; for example, at or near the center of the platform surface but it is not required. In some embodiments, sample gemstones are placed at different locations on the platform surface. A plurality of color images of the gemstone are then taken at different image rotational angles. In preferred embodiments, the angular difference between consecutive color images remains constant throughout the collection of all images. Any configurations disclosed herein (e.g., concerning image view angles and image rotational angles) can be applied to the image collection process. For example, if the camera is set up to take 30 pictures per second and one full rotation of the sample platform takes 3 seconds, 90 images will be collected after a full rotation. In some embodiments, platform surface completes at least a full rotation with respect to the image capturing component. In some embodiments, the rotation is less than a full rotation. In some embodiments, the rotation is more than a full rotation; for example, 1.2 full rotations or less, 1.5 full rotations or less, 1.8 full rotations or less, 2 full rotations or less, 5 rotations, or 10 full rotations or less.

At step 924, an outline mask is extracted for each image. Generally, an outline mask corresponds to the physical area occupied by a sample gemstone, represented by the full image of the sample gemstone. FIGS. 7A and 7B illustrate the differences for an image of the same diamond, before and after an outline mask is applied. As depicted in FIG. 7B, the outline mask highlights and clearly defines the edges of the diamond such that parameters like width and height can be more easily measured.

There are many methods for edge detection, and most of them can be grouped into two categories, search-based and zero-crossing based. The search-based methods detect edges by first computing a measure of edge strength, usually a first-order derivative expression such as the gradient magnitude, and then searching for local directional maxima of the gradient magnitude using a computed estimate of the local orientation of the edge, usually the gradient direction. The zero-crossing based methods search for zero crossings in a second-order derivative expression computed from the image in order to find edges, usually the zero-crossings of the Laplacian or the zero-crossings of a non-linear differential expression.

The edge detection methods known to date mainly differ in the types of smoothing filters that are applied and the way the measures of edge strength are computed. As many edge detection methods rely on the computation of image gradients, they also differ in the types of filters used for computing gradient estimates in the x- and y-directions.

Here, any applicable method for extracting an outline mask can be used, including for example an edge determining filter in commercially available software products such as Photoshop™ and etc. Additionally, for example, a simple algorithm can be developed in which any continuous areas in an image with a color value matching the background white color (as previously calibrated) is defined as black. As a result, a continuous black area will form the outline mask with an opening corresponding to the full image of a sample gemstone.

At step 926, for each opening area corresponding to the full image of a sample gemstone, values of geometrical parameters (e.g., the width and height of the gemstone as illustrated in FIG. 7B) are determined. Outline masks are used for more accurate or automated measurements of the geometrical parameters. Essentially, the geometrical parameters are determined based on each outline mask, or more precisely, the opening of each outline mask. The measurements are taken for each image. After this step, a plurality set of measurement values are determined for the plurality of color images (or their corresponding outline masks), including, for example, a plurality of width measurements and a plurality of height measurements.

Figure 11A:
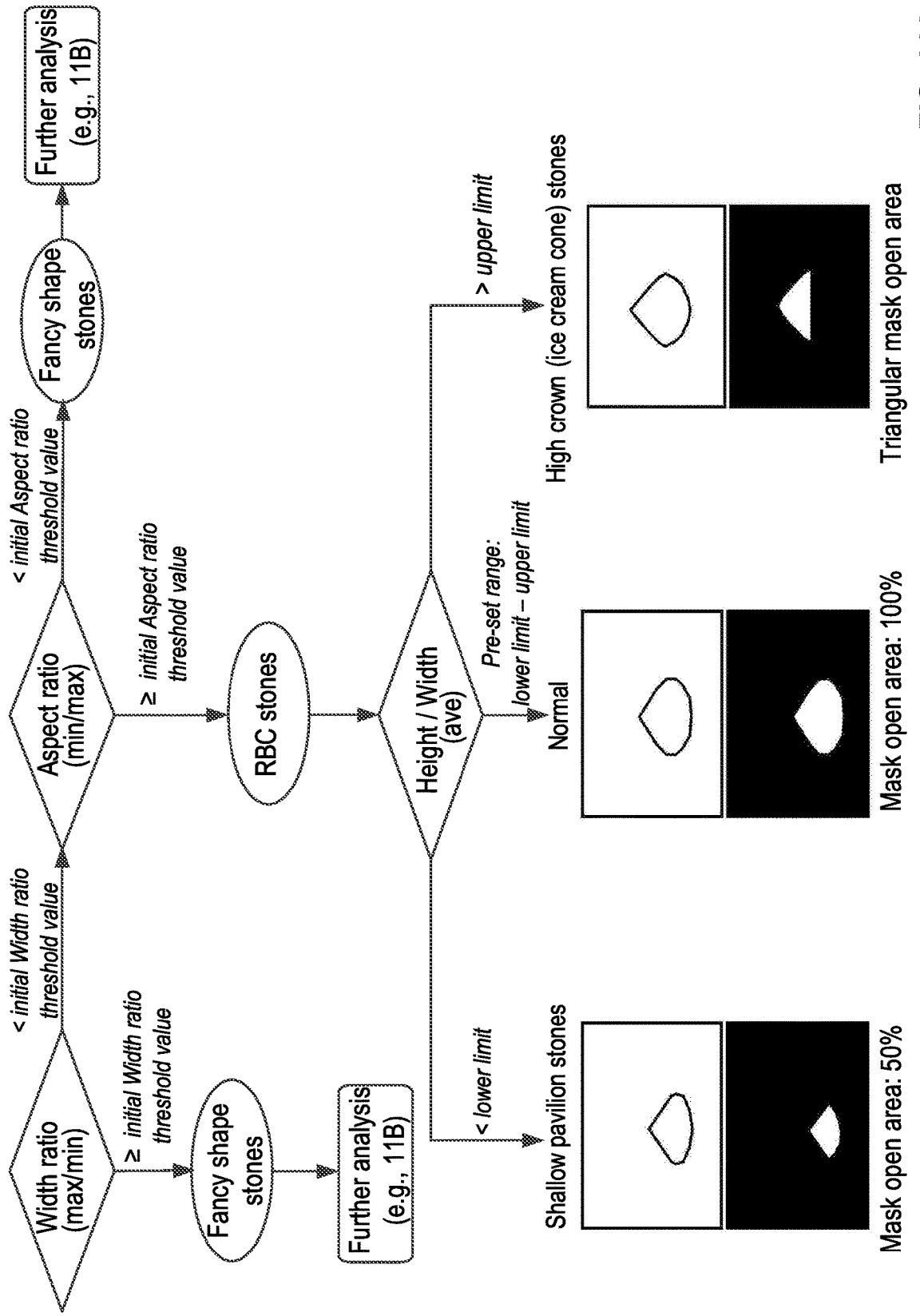
FIG. 11A depicts an exemplary classification process.

At step 928, one or more proportion or shape characteristics are defined. For example, among the plurality of width measurements, the maximum width and the minimum width are identified. $Width_{max}$ is the maximum width identified among the plurality of outline masks and $Width_{min}$ is the minimum width diamond width identified among the outline masks. The characteristic, $Width_{max}/Width_{min}$, is defined as the ratio of the maximum width versus the minimum width. Also for example, an aspect ratio (defined as the ratio of height versus width: Height/Width) can be determined for each image (or outline mask). The characteristic, $Aspect_{max}/Aspect_{min}$, is defined as the ratio of the minimum aspect ratio versus the maximum aspect ratio. In some embodiments, average aspect ratios are also calculated and used as a proportion or shape characteristic. Another example of a shape or proportion characteristic is an average of aspect ratio; or average Height/Width. In some embodiments, the Width ratio (e.g., $Width_{max}/Width_{min}$) and Aspect ratio (e.g., $Aspect_{max}/Aspect_{min}$) of a sample gemstone, alone or in combinations, are used to classify the sample gemstone, for example, for the purpose of selecting a region within the gemstone for further color analysis. In some embodiments, when the Width ratio (e.g., $Width_{max}/Width_{min}$) is greater than an initial Width ratio threshold value, the gemstones are significantly asymmetrical and will be defined as fancy shape gemstones (FIG. 11A). In such embodiments, a $Width_{max}/Width_{min}$ threshold value is 1.05 or greater; 1.1 or greater; 1.15 or greater; 1.2 or greater; 1.25 or greater, 1.3 or greater; 1.35 or great, or 1.4 or greater.

In some embodiments, the non-fancy stones are subject to further analysis. For example, when the Aspect ratio (e.g., $Aspect_{max}/Aspect_{min}$) is smaller than an initial Aspect ratio threshold value, the gemstones are flatter than a regular RBC and will also be defined as fancy shape gemstones (FIG. 11A). In such embodiments, a $Aspect_{max}/Aspect_{min}$ threshold is less than 0.95; less than 0.9; less than 0.85; less than 0.8; less than 0.75; less than 0.7; less than 0.65; or less than 0.6. In some embodiments, gemstones that are classified as regular gemstones after Aspect ratio analysis (e.g., RBC gemstones such as diamonds) are subject to further classification; for example, using the average Aspect ratio as a parameter. When the average Aspect ratio of a gemstone (e.g., a diamond) is between a predetermined range, the gemstone will be classified as normal RBC (FIG. 11A). When the average Aspect ratio of a gemstone (e.g., a diamond) is greater than the upper limit of the predetermined range, the gemstone is classified as having unusual shape (e.g., a high crown or ice cream cone shaped diamond). Similarly, when the average Aspect ratio of a gemstone (e.g., a diamond) is smaller than the lower limit of the predetermined range, the gemstone is also classified as having unusual shape (e.g., a diamond with a shallow pavilion). In some embodiments, the upper limit of the predetermined range is between 0.6 and 0.9; more preferably between 0.6 and 0.8 or between 0.7 and 0.85. In some embodiments, the lower limit of the predetermined range is between 0.4 and 0.7; more preferably between 0.5 and 0.7 or between 0.55 and 0.65.

Figure 11B:
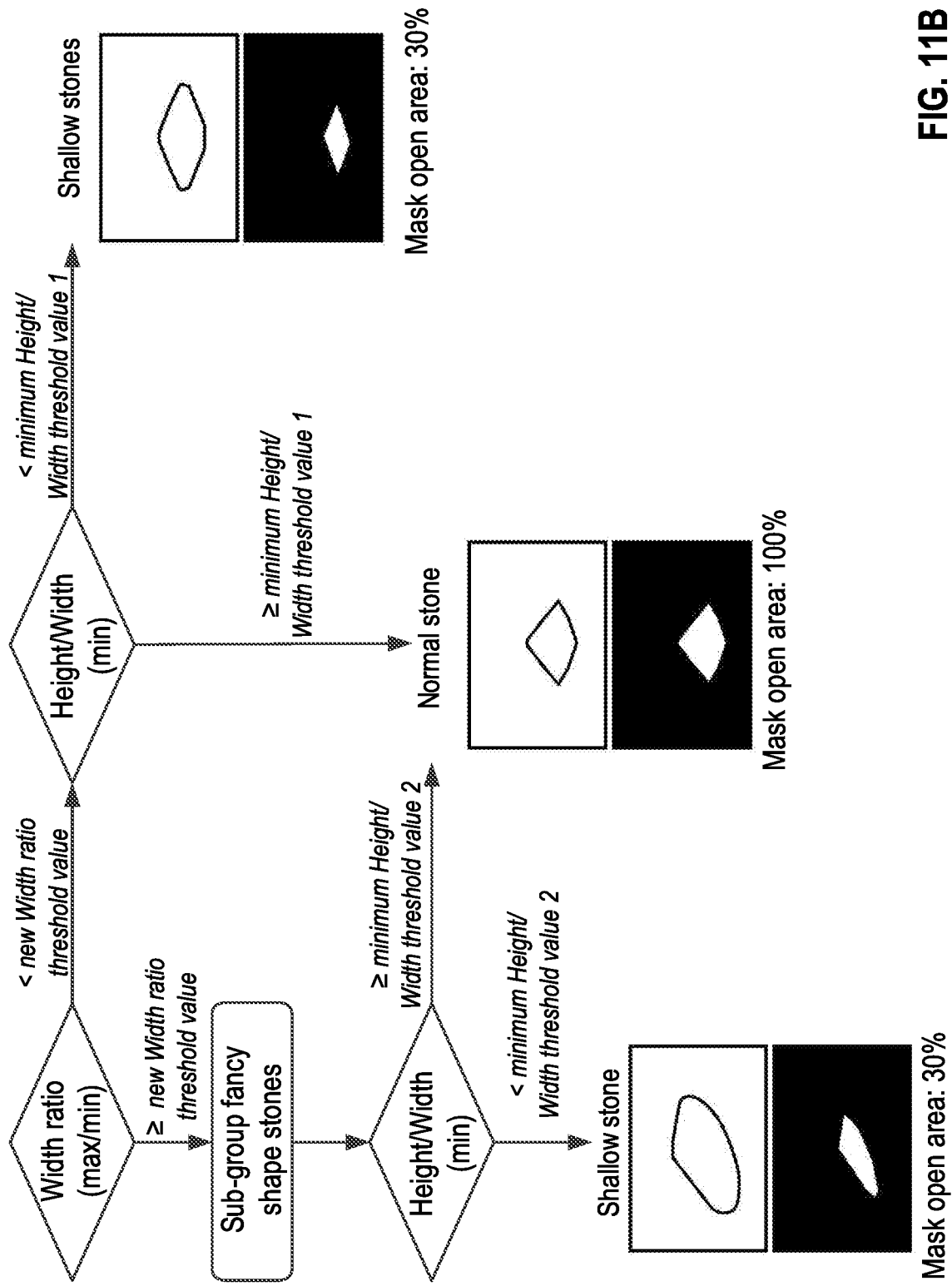
FIG. 11B depicts an exemplary re-classification process.

In some embodiments, gemstones that are classified as fancy stones (e.g., based on the exemplary algorithm in FIG. 11A) are further classified. For example, a new Width ratio (e.g., $Width_{max}/Width_{min}$) threshold is selected (FIG. 11B). Based on this new threshold value, the fancy gemstones are classified into two groups: those with a Width ratio higher than the new Width ratio threshold value and those with a Width ratio lower than the new Width ratio threshold value. The new Width ratio threshold value is higher than the previous Width ratio threshold value; at for example, 1.2 or greater; 1.25 or greater, 1.3 or greater; 1.35 or great, 1.4 or greater, 1.45 or greater, or 1.5 or greater.

In some embodiments, the further classified gemstones are subject to still further classification; for example, by examining their Aspect ratios (FIG. 11B). Gemstones with a Width ratio higher than the new Width ratio threshold value are further classified based on their minimum Aspect ratios (e.g., the minimum Height/Width ratio). These gemstones are classified into two groups using a first minimum Height/Width ratio threshold value. Gemstones with a minimum Aspect ratio at or higher than first minimum Height/Width ratio threshold value are re-classified as normal stones. Gemstones with a minimum Aspect ratio lower than first minimum Height/Width ratio threshold value are re-classified as shallow stones (FIG. 11B). In some embodiments, the first minimum Height/Width ratio threshold value is 0.6 or smaller; 0.55 or smaller; 0.5 or smaller; 0.45 or smaller; 0.4 or smaller; 0.35 or smaller; 0.3 or smaller; 0.25 or smaller; or 0.2 or smaller. Gemstones with a Width ratio lower than the new Width ratio threshold value are also further classified based on their minimum Aspect ratios (e.g., the minimum Height/Width ratio) (FIG. 11B). These gemstones are classified into two groups using a second minimum Height/Width ratio threshold value. Gemstones with a minimum Aspect ratio at or higher than second minimum Height/Width ratio threshold value are re-classified as normal stones. Gemstones with a minimum Aspect ratio lower than second minimum Height/Width ratio threshold value are re-classified as shallow stones (FIG. 11B). In some embodiments, the second minimum Height/Width ratio threshold value is 0.7 or smaller; 0.65 or smaller; 0.6 or smaller; 0.55 or smaller; 0.5 or smaller; 0.45 or smaller; 0.4 or smaller; 0.35 or smaller; 0.3 or smaller; 0.25 or smaller; or 0.2 or smaller.

Referring back to FIG. 9A, at step 930, depending on the values of proportional characteristics such as a $Width_{max}/Width_{min}$ ratio, a $Aspect_{max}/Aspect_{min}$ ratio, an average or minimum aspect ratio, a defined area will be selected within a full image of the sample gemstone. The defined area is selected by applying a virtual mask having an open area that corresponds to a portion of the open area in the corresponding outline mask. The information within the defined area will be subject to further color analysis.

In some embodiments, a defined area or a virtual mask is calculated by proportionally shrinking the corresponding outline mask without changing the weighed center. In some embodiments, a virtual mask is created by selected color area with specific range of color parameters. For example, only areas with an R, G, or B component having values in the specified range will be included to form the virtual mask. In some embodiments, instead of ranges, predetermined threshold values can be used for selecting color areas; i.e., only areas with an R, G, or B component having values above or below the threshold will be included to form the virtual mask. In some embodiments, two color components are used in the evaluation. In some embodiments, all three color components are used in the evaluation. Other parameters that can be used in defining the virtual mask include but are not limited to L*, a*, b*, h, C, M, Y, K, and etc. It will be understood that each color parameter can be used alone or in any combination with one or more other color components.

In some embodiments, a selected portion of the sample gemstone is used to define the virtual mask. For example, for a diamond of round brilliant cut (RBC) but with a high crown (i.e., the ice cream cone type RBC), only the top pavilion part is considered in further analysis by applying a triangular virtual mask to only the top portion of the diamond.

In some embodiments, the defined area (e.g., the open area of a virtual mask) corresponds to the entire sample gemstone (e.g., outline mask). In some embodiments, the defined area corresponds to a portion of the entire sample gemstone. In some embodiments, the defined area corresponds to an upper portion of the sample gemstone. In some embodiments, the defined area corresponds to a middle portion of the sample gemstone. In some embodiments, the defined area corresponds to a lower portion of the sample gemstone.

In some embodiments, the defined area corresponds to 20% or less of the entire gemstone, 25% or less of the entire gemstone, 30% or less of the entire gemstone, 35% or less of the entire gemstone, 40% or less of the entire gemstone, 45% or less of the entire gemstone, 50% or less of the entire gemstone, 55% or less of the entire gemstone, 60% or less of the entire gemstone, 65% or less of the entire gemstone, 70% or less of the entire gemstone, 75% or less of the entire gemstone, 80% or less of the entire gemstone, 85% or less of the entire gemstone, 90% or less of the entire gemstone, 95% or less of the entire gemstone, or 100% or less of the entire gemstone. For example, in some embodiments, the defined area in a normal RBC cut diamond corresponds to 100% of the entire gemstone. In some embodiments, the defined area in an RBC cut diamond with a shallow pavilion corresponds to only 50% of the entire gemstone. In some embodiments, the defined area in an RBC cut diamond with a high crown corresponds to only the triangle part of the pavilion area. As described above, in some embodiments gemstones go through further analysis and are re-classified. In some embodiments, the defined area in a re-classified normal stones corresponds to 100% of the entire gemstone. In some embodiments, the defined area in a re-classified shallow stone corresponds to only 30% of the entire gemstone.

The defined area can be in any shape. In some embodiments, the defined area is a triangle. In some embodiments, the defined area is an oval, a circle, or a rectangle. In some embodiments, the defined area has an irregular shape, such as an area with four sides, five sides, and etc. In some embodiments, the defined area has a curved feature, such as an oval, a circle or an irregular curved shape. In some embodiments, the defined area has a combination of straight-lined and curved features. For example, the defined area can be a triangle with a curved side.

Figure 10:
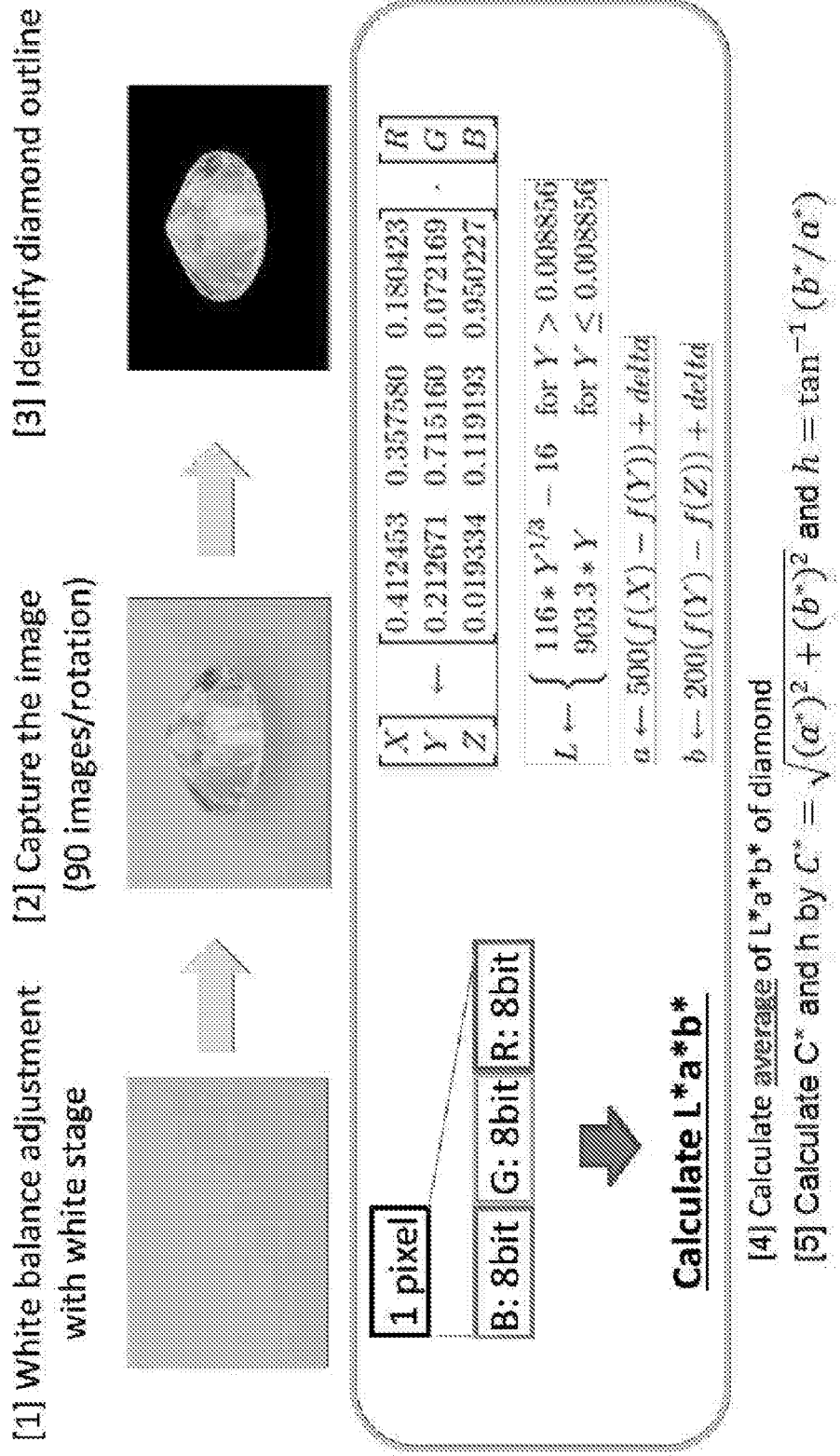
FIG. 10 depicts an exemplary analytical process.

At step 940, pixels within the defined area are subject to quantitative analysis. For example, each pixel can be analyzed to quantify the values of all color components in the particular pixel. The number of color component is determined by the algorithm according to which the pixel is encoded when the color image is first captured. In some embodiments, the image is converted from its capturing color mode (e.g., CMYK) to a different color mode (e.g., RGB). Values for the individual color components are then converted to one or more parameters representing the color characteristic of each pixel. In some embodiments, RGB values are converted to CIE (Commission Internationale de l'Eclairage or International Commission on Illumination) color space values such as (L*, a*, b*). An exemplary conversion process is depicted in FIG. 10.

At step 950, the conversion process is carried out for all pixels within a defined area in an image in order to calculate average values of the one or more parameters. The steps of 910-950 can be repeated for all images in the plurality of color images. Eventually, average values of the one or more parameters (e.g., L*, a*, and b*) can be calculated for each color component based on information from all images.

At step 960, one or more color scores are calculated based on the values of the one or more parameters. For example, in some embodiments, CIE color space values (e.g., L*, a*, and b*) are converted to additional color score such as chroma (C*) and hue (h) values; e.g., based on the following equations (FIG. 10):

$$C* = \sqrt{(a*)^2 + (b*)^2}$$

$$h = \tan^{-1}\left(\frac{b*}{a*}\right)$$

In some embodiments, color images are analyzed using the standards (e.g., tables of color matching functions and illuminants as a function of wavelength) published by CIE. A plot of the standard daylight illuminant with a correlated color temperature of 6500 K, $D_{65}$. This illuminant is represented here by the function $H_{D65}(\lambda)$. The color matching functions: $\bar{x}(\lambda)$, $\bar{y}(\lambda)$, $\bar{z}(\lambda)$ are used to calculate colorimetry parameters.

At step 970, values of color scores, e.g., L*, C*, h* are compared to previously determined standard values to give a color grade to the sample gemstone. The previously determined standard values are obtained using the same or a similar process. For example, one or more sets of sample stones, which share the same or similar proportion or shape characteristic and whose color grading values have been previously determined, are used as the grading standards.

An example of computing color characteristics is as follows. As diamond is a transparent material, the sum of transmission spectrum $T(\lambda)$ and reflection spectrum $R(\lambda)$ is used in the calculation of the tristimulus values, X, Y and Z:

$$X\Sigma_{\lambda=380}^{780} H_{D65}(\lambda)(T(\lambda)+R(\lambda))\bar{x}(\lambda)$$

$$Y\Sigma_{\lambda=380}^{780} H_{D65}(\lambda)(T(\lambda)+R(\lambda))\bar{y}(\lambda)$$

$$Z\Sigma_{\lambda=380}^{780} H_{D65}(\lambda)(T(\lambda)+R(\lambda))\bar{z}(\lambda)$$

The chromaticity coordinates, x and y, are then defined as:

$$x = \frac{X}{X+Y+Z}$$

$$y = \frac{Y}{X+Y+Z}$$

An attempt to achieve a "perceptually uniform" colour space is the CIE 1976 colour space, otherwise known as the CIELAB colour space. Its parameters are calculated from the tristimulus values as follows: lightness, $L*=116 (Y/Y_W)^{1/3}-16$ red-green parameter, $a*=500[(X/X_W)^{1/3}-(Y/Y_W)^{1/3}]$ and yellow-blue parameter, $b*=200 [(Y/Y_W)^{1/3}-(Z/Z_W)^{1/3}]$, where $X_W$, $Y_W$ and $Z_W$ are the tristumulus values for the white point corresponding to the chosen illuminant, in this case D65.

$$X_w = \sum_{\lambda=380}^{780} H_{D65}(\lambda)\bar{x}(\lambda)$$

$$Y_w = \sum_{\lambda=380}^{780} H_{D65}(\lambda)\bar{y}(\lambda)$$

$$Z_w = \sum_{\lambda=380}^{780} H_{D65}(\lambda)\bar{z}(\lambda)$$

The saturation or chroma is expressed as: $C*_{ab}=(a*^2+b*^2)^{1/3}$ and the hue angle is expressed as: $h_{ab}=\tan^{-1}(b*/a*)$.

Sources are available for image/color conversion and transformation. For example the Open CV project hosted at the docs<dot>opencv<dot>org can be used to convert RGB values to CIE L, a, b values. In addition, the same or similar resources allows conversion between RGB values and hue-saturation-value (HSV) values, between RGB values and hue-saturation-lightness (HSL) values, between RGB values and CIE Luv values in the Adams chromatic valence color space.

In another aspect, the methods and systems disclosed herein are used to detect or evaluate changes of color properties of a sample gemstone over time. For example, the color of a gemstone may change over time. Also, the intensity of the color of a gemstone may change over time.

In such embodiments, multiple sets or pluralities of images (e.g., color images) are collected of a gemstone over a period of time. For example, using the system disclosed herein, each set of images is collected automatically over multiple image angles. There is no limitation as to how much sets of image can be collected over time, for example, two or more sets of images; three or more sets of images; four or more sets of images; five or more sets of images; six or more sets of images; seven or more sets of images; eight or more sets of images; nine or more sets of images; 10 or more sets of images; 15 or more sets of images; 20 or more sets of images; 30 or more sets of images; 50 or more sets of images; or 100 or more sets of images can be collected.

In some embodiments, all sets of images are collected of the same gemstone by applying the same system configuration; for example, using the same camera, same image angle, same reflector, same platform and etc.

Among the multiple sets of images, two consecutive sets of images are separately for a time gap ranging from minutes to hours or even days, depending on the nature of the color change of the stone. The duration of the time gap is determined by how quickly color changes may take place in the sample stone. There is no limitation as to how long or how short the time gap can be. For example, the time gap can be two minutes or shorter; five minutes or shorter; 10 minutes or shorter; 20 minutes or shorter; 30 minutes or shorter; 60 minutes or shorter; 2 hours or shorter; 5 hours or shorter; 12 hours or shorter; 24 hours or shorter; 2 days or shorter; 5 days or shorter; or 10 days or shorter.

In some embodiments, calculations are done for each set of images to assign a color grade for the sample gemstone. Color grades from multiple sets of images are then compared to determine color change over time.

The present invention can be implemented as a computer system and/or a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Instrument Color Grading of Cape Yellow Stones

FIGS. 12A and 12B depicts the grading results of 3 cape yellow stones. FIG. 12A shows that a mask with an opening matching the entire gemstone was used in computing the color grade values for sample 1. Here the L, a, b, C, H values are calculated based on instrumental analysis disclosed herein.

The grading results for samples 1 through 3 are summarized in the Table in FIG. 12B. Here, the instrumental color grades for samples 1, 2, 3 are D, F and J, which matched the grades provided by visual grading according to experience human grader(s).

The results shown here support that color grading by instruments described herein is consistent with visual grading by human graders over a wide range of color quality.

Example 2

Instrument Color Grading of Stones of Unusual Colors

The table in FIG. 13 shows the results of color grading results of stones of unusual or off colors. A gemstone is off color if the presence of a particular color is weak or if there are multiple colors present.

Samples 4 through 7 include stones that are bluish, pinkish, brownish and greenish yellow. Once again, masks with an opening matching the entire gemstones were used in computing the color grade values for sample 4, sample 5, sample 6 and sample 7.

For bluish diamond (sample 4) both human grader and our instrument provided a color grade of E. For pinkish diamond (sample 5) both human grader and our instrument provided a color grade of F. For brown diamond (sample 6) both human grader and our instrument provided a color grade of Y/Z. For greenish yellow diamond (sample 7) both human grader and our instrument provided a color grade of F.

The result shown here supports that color grading by instruments described herein is consistent with visual grading by human graders for low color grade gemstone.

Example 3

Instrument Color Grading of Fancy Shape Stones

The table in FIG. 15 summarizes the color grading results of 3 exemplary fancy shape stones. Again, masks with an opening matching the entire gemstones were used in computing the color grade values for sample 8, sample 9 and sample 10. Here, instrument grading once again provided color grades that are consistent with those provided by experience human graders.

These examples show that gemstones that are initially classified as fancy shape stones can still be subject to a normal mask analysis; i.e., using a mask having an opening that matches the entire gemstone (see, for example, FIG. 11B).

Example 4

Effects of Mask Adjustment Based on Proportion or Shape

This example illustrates the effects of mask adjustment on proper color grading. The grading results are summarized in the table in FIG. 15. Sample 11 is a stone with high depth. According to human grading, the color grade is J. When a mask with an opening corresponding to the entire gemstone area (100%) was used, instrumental color analysis provided a color grade of L, significantly different from the human grading result. However, when the mask open area was adjusted to a triangle that covered only a portion of the stone (for example, the top portion as illustrated in FIG. 11A), the color grade obtained from instrument analysis became J, consistent with the result of human grading.

Sample 12 is a stone with a low depth stone. According to human grading, the color grade is H. When a mask with an opening corresponding to the entire gemstone area (100%) was used, instrumental color analysis provided a color grade of I, significantly different from the human grading result. However, when the mask open area was adjusted to a smaller area that covered only a portion of the stone (for example, the top 50% as illustrated in FIG. 11A), the color grade obtained from instrument analysis became H, consistent with the result of human grading.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

We claim:

1. An apparatus for assessing a color characteristic of a gemstone, comprising:
    an optically opaque platform, wherein the platform has a surface configured for supporting a gemstone;
    a daylight-approximating light source at color temperature 6500 K, D65 shaped to at least partially enclose the platform, wherein the light source is located at the same level as or below the platform and is designed to provide uniform diffused illumination to the gemstone on the platform;
    a reflector having an inner surface that is at least partially spherical and comprises a reflective material, wherein the reflector at least partially covers the light source and platform surface, and reflects illumination from the light source towards the gemstone positioned on the platform surface;
    a camera and telecentric lens, wherein the camera and platform are configured to rotate relative to each other and capture color images of the gemstone; and
    a computer with a processor and memory in communication with the camera, the computer configured to,
    receive multiple color images captured by the camera of the gemstone,
        wherein the received multiple color images are in Cyan, Magenta, Yellow, and Key (CMYK) color mode,
    convert each pixel in a first area of a first received image of the multiple color images in the CMYK color mode images to Red Green Blue (RGB) color mode,
    convert the first converted RGB color mode for the first received image pixels to Commission Internationale de l'Elcairage (CIE) color space values of L*, a* and b*;
    convert each pixel in a second area of a second received image of the multiple color images in the CMYK color mode images to RGB color mode,
    convert the second converted RGB color mode for the second received image pixels to CIE color space values of L*, a* and b*,
    convert the CIE color space values of lightness L*, a* and b* to chroma (C*) and hue (h*) values, and
    compare the L*, C* and h* values to previously determined standard values to determine a color grade for the gemstone.

2. The apparatus of claim 1, wherein the camera is positioned at an angle 65 degrees or smaller as measured, relative to the platform surface that supports the gemstone.

3. The apparatus of claim 1, wherein the telecentric lens comprises an object-space telecentric lens, or a double telecentric lens.

4. The apparatus of claim 1, wherein the platform is configured to rotate about a rotational axis that is perpendicular to the surface of the platform where the gemstone is supported.

5. The apparatus of claim 1 wherein the angle between the camera and the platform surface is between approximately zero and approximately 45 degrees.

6. The apparatus of claim 1, wherein the platform surface comprises a reflective or a diffuser material.

7. The apparatus of claim 1, wherein the daylight-approximating light source is configured as a ring light surrounding the platform surface.

8. The apparatus of claim 1, wherein the daylight-approximating light source is selected from the group consisting of one or more halogen lamps with a color balancing filter, multiple light emitting diodes arranged in a ring-like structure surrounding the platform surface, fluorescence lamp, Xe lamp, Tungsten lamp, metal halide lamp, laser-induced white light (LDLS), and combinations thereof.

9. The apparatus of claim 1, wherein the camera is selected from the group consisting of a color camera, a CCD camera, and one or more CMOS sensor arrays.

10. The apparatus of claim 1, wherein the platform is made of a material selected from the group consisting of polytetrafluoroethylene (PTFE), fluoropolymer, barium sulfate, Gold, Magnesium Oxide, and combinations thereof.

11. The apparatus of claim 1 wherein the angle between the camera and the platform surface is between approximately 10 degrees and approximately 35 degrees.

12. The apparatus of claim 1, wherein the platform surface comprises a reflective material.

13. The apparatus of claim 1, wherein the platform surface comprises a diffuse reflective material.

14. The apparatus of claim 1, wherein the platform surface comprises a white diffuse reflective material.

15. The apparatus of claim 1 wherein the computer is further configured to calculate an average color space value of L*, a* or b* using the CIE color space values from the first received image and the second received image.

16. The apparatus of claim 15 wherein the computer is further configured to determine a color score for the gemstone based on the calculated average color space value of L*, a* or b*.

* * * * *